United States Patent
Lin et al.

(10) Patent No.: US 9,777,273 B2
(45) Date of Patent: Oct. 3, 2017

(54) SMALL INTERFERING RNA AND PHARMACEUTICAL COMPOSITION AND METHOD FOR INHIBITING GALECTIN-12 EXPRESSION AND/OR ENHANCING LIPOLYSIS CONTAINING THE SAME

(71) Applicants: Industrial Technology Research Institute, Hsinchu (TW); Academia Sinica, Taipei (TW)

(72) Inventors: Yen-Ju Lin, Taichung (TW); Jui-Wen Huang, Fenyuan Township (TW); Fu-Tong Liu, Taipei (TW); Huan-Yuan Chen, Taipei (TW); Wei-Chen Hsieh, Taipei (TW)

(73) Assignees: INDUSTRIAL TECHNOLOGY RESEARCH INSTITUTE, Hsinchu (TW); ACADEMIA SINICA, Taipei (TW)

( * ) Notice: Subject to any disclaimer, the term of this patent is extended or adjusted under 35 U.S.C. 154(b) by 0 days.

(21) Appl. No.: 15/322,878

(22) PCT Filed: Aug. 5, 2015

(86) PCT No.: PCT/US2015/043761
§ 371 (c)(1),
(2) Date: Dec. 29, 2016

(87) PCT Pub. No.: WO2016/022648
PCT Pub. Date: Feb. 11, 2016

(65) Prior Publication Data
US 2017/0159051 A1    Jun. 8, 2017

Related U.S. Application Data

(60) Provisional application No. 62/034,434, filed on Aug. 7, 2014.

(51) Int. Cl.
*C12N 15/11* (2006.01)
*C12N 15/113* (2010.01)

(52) U.S. Cl.
CPC ........ *C12N 15/113* (2013.01); *C12N 2310/14* (2013.01); *C12N 2310/315* (2013.01); *C12N 2310/321* (2013.01)

(58) Field of Classification Search
None
See application file for complete search history.

(56) References Cited

U.S. PATENT DOCUMENTS

| | | |
|---|---|---|
| 2003/0208044 A1 | 11/2003 | Ni et al. |
| 2005/0250123 A1 | 11/2005 | Yang et al. |
| 2010/0098683 A1 | 4/2010 | Kufe |
| 2015/0126583 A1* | 5/2015 | Liu ................. C12N 15/113 514/44 A |

FOREIGN PATENT DOCUMENTS

| | | |
|---|---|---|
| WO | WO 2005/116204 A1 | 12/2005 |
| WO | WO 2013/075132 A1 | 5/2013 |
| WO | WO 2013/052444 A1 | 11/2013 |

OTHER PUBLICATIONS

International Search Report, issued in PCT/US2015/043761, dated Jan. 5, 2016.
Written Opinion of the International Searching Authority, issued in PCT/US2015/043761, dated Jan. 5, 2016.

* cited by examiner

*Primary Examiner* — Kate Poliakova-Georgantas
(74) *Attorney, Agent, or Firm* — Birch, Stewart, Kolasch & Birch, LLP

(57) ABSTRACT

A small interfering RNA is provided. The small interfering RNA consists of a passenger strand and a guide strand, wherein the sequence of the passenger strand comprises the sequence of SEQ ID NO. 7, and the sequence of the guide strand comprises the sequence of SEQ ID NO. 8, wherein the small interfering RNA is capable of inhibiting galectin-12 expression.

21 Claims, 11 Drawing Sheets

SMALL INTERFERING RNA AND PHARMACEUTICAL COMPOSITION AND METHOD FOR INHIBITING GALECTIN-12 EXPRESSION AND/OR ENHANCING LIPOLYSIS CONTAINING THE SAME

CROSS REFERENCE TO RELATED APPLICATION

This application is the National Phase of PCT International Application No. PCT/US2015/043761, filed on Aug. 5, 2015, which claims priority under 35 U.S.C. 119(e) to U.S. Provisional Application No. 62/034,434, filed on Aug. 7, 2014, all of which are hereby expressly incorporated by reference into the present application.

JOINT RESEARCH AGREEMENT

The present disclosure was made by or on behalf of the below listed parties to a joint research agreement. The joint research agreement was in effect on or before the date the present disclosure was made, and the present disclosure was made as a result of activities undertaken within the scope of the joint research agreement. The parties to the joint research agreement are 1) Industrial Technology Research Institute and 2) Academia Sinica.

INCORPORATION BY REFERENCE OF SEQUENCE LISTING

A sequence listing submitted as a text file via EFS-Web is incorporated herein by reference. The text file containing the sequence listing is named "0965-A24560-PCT-XX_Seq_Listing.txt"; its date of creation was Aug. 3, 2015; and its size is 18,936 bytes.

TECHNICAL FIELD

The technical field relates to a small interfering RNA and a pharmaceutical composition and a method for inhibiting galectin-12 expression and/or enhancing lipolysis containing the same.

BACKGROUND

Galectin-12 is preferentially expressed in adipocytes and is a member of the β-galactoside-binding lectin family. Galectin-12 regulates lipolysis (lipid degradation) by modulating lipolytic protein kinase A (PKA) signaling. It has verified that deficiency of galectin-12 in animals results in enhanced adipocyte lipolysis, increased mitochondria respiration, reduced adiposity and ameliorated insulin resistance associated with weight gain. Accordingly, galectin-12 may be a useful target for treatment of obesity-related metabolic conditions, such as insulin resistance, metabolic syndrome, and type 2 diabetes.

Small interfering RNA (siRNA) is a class of double-stranded RNA molecules with 20-25 base pairs in length, which sometimes are known as short interfering RNA or silencing RNA. siRNA plays many roles, but it is most notable in the RNA interference (RNAi) pathway, where it interferes with the expression of specific genes with complementary nucleotide sequences. siRNA functions by causing mRNA to be broken down after transcription, resulting in no translation.

Use of small interfering RNA (siRNA) for treatment of obesity-related metabolic conditions has not been reported.

SUMMARY

The present disclosure provides a small interfering RNA, comprising: (a) a first small interfering RNA consisting of a first passenger strand and a first guide strand, wherein the sequence of the first passenger strand is a sequence with at least 85% sequence identity to the sequence of SEQ ID NO. 1, and the sequence of the first guide strand is a sequence with at least 85% sequence identity to the sequence of SEQ ID NO. 2; (b) a second small interfering RNA consisting of a second passenger strand and a second guide strand, wherein the sequence of the second passenger strand is a sequence with at least 85% sequence identity to the sequence of SEQ ID NO. 3, and the sequence of the second guide strand is a sequence with at least 85% sequence identity to the sequence of SEQ ID NO. 4; (c) a third small interfering RNA consisting of a third passenger strand and a third guide strand, wherein the sequence of the third passenger strand is a sequence with at least 85% sequence identity to the sequence of SEQ ID NO. 5, and the sequence of the third guide strand is a sequence with at least 85% sequence identity to the sequence of SEQ ID NO. 6; or (d) a fourth small interfering RNA consisting of a fourth passenger strand and a fourth guide strand, wherein the sequence of the fourth passenger strand is a sequence with at least 85% sequence identity to the sequence of SEQ ID NO. 7, and the sequence of the fourth guide strand is a sequence with at least 85% sequence identity to the sequence of SEQ ID NO. 8, wherein the small interfering RNA is capable of inhibiting galectin-12 expression.

The present disclosure also provides a pharmaceutical composition for inhibiting galectin-12 expression and/or enhancing lipolysis, comprising: the small interfering RNA as mentioned above.

The present disclosure further provides a method for inhibiting galectin-12 expression and/or enhancing lipolysis, comprising: administering the pharmaceutical composition mentioned above to a subject in need.

A detailed description is given in the following embodiments with reference to the accompanying drawings.

BRIEF DESCRIPTION OF DRAWINGS

The present disclosure can be more fully understood by reading the subsequent detailed description and examples with references made to the accompanying drawings, wherein.

Figure 2A:
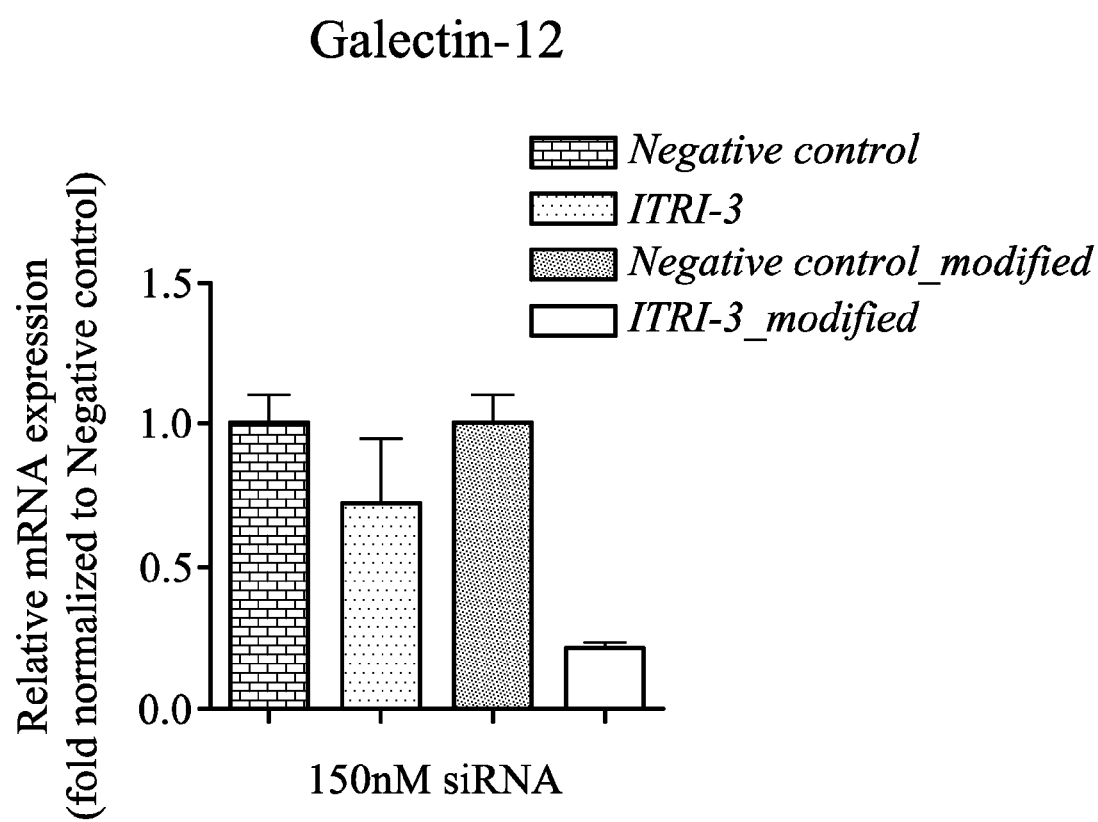
FIG. 2A shows mRNA expression levels of galectin-12 of NIH-3T3-L1 cell derived adipocytes transfected with negative control siRNA (unmodified form and modified form)
Figure 2B:
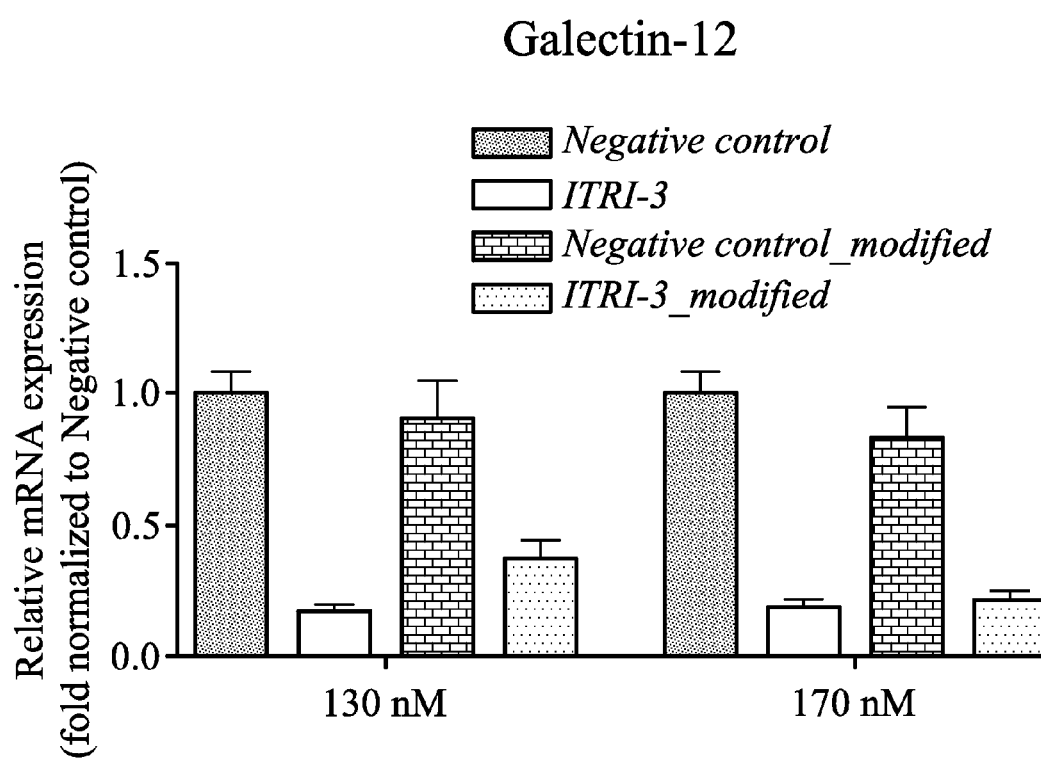
Figure 2C:
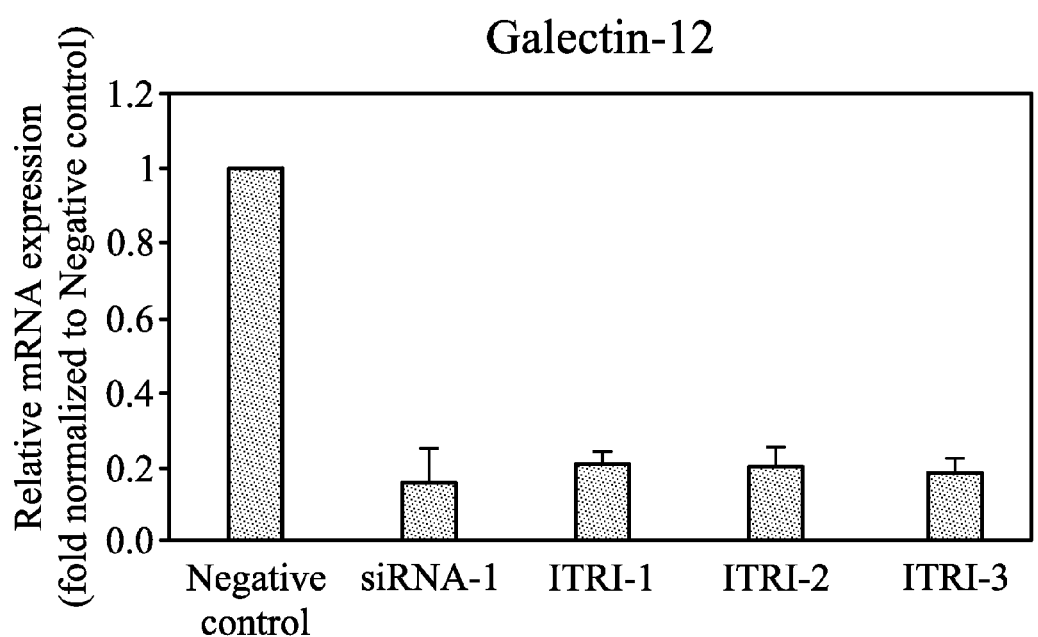
Figure 3:
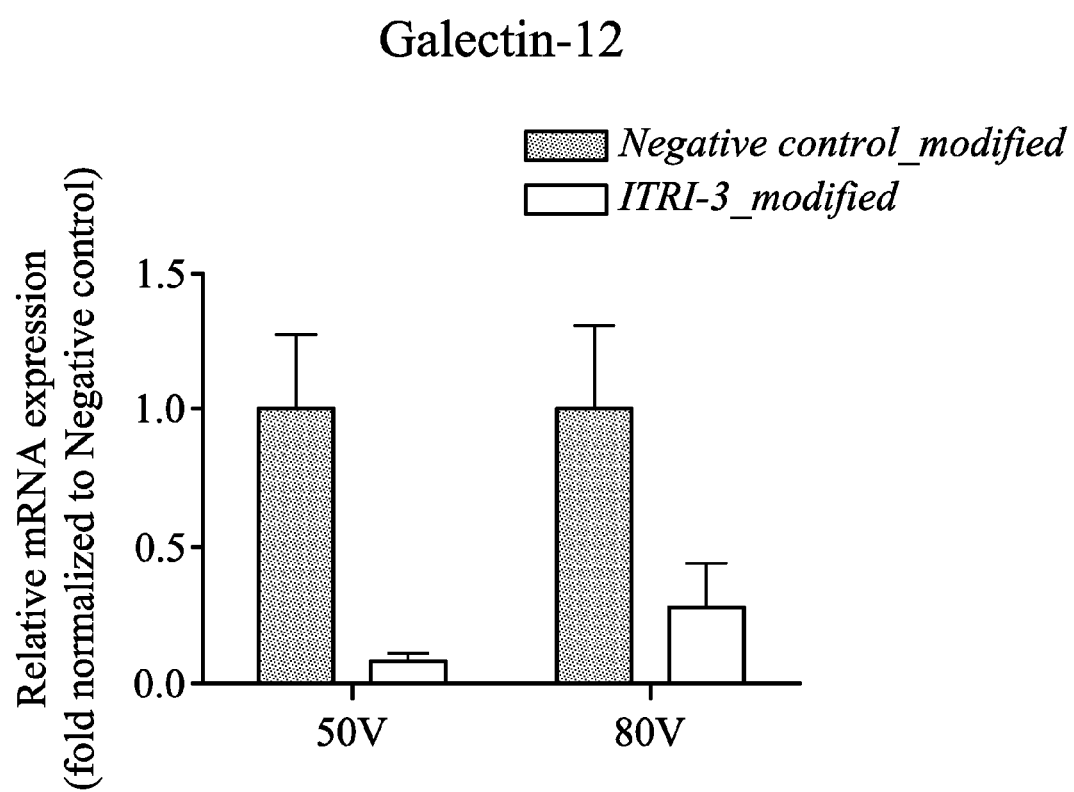
Figure 4:
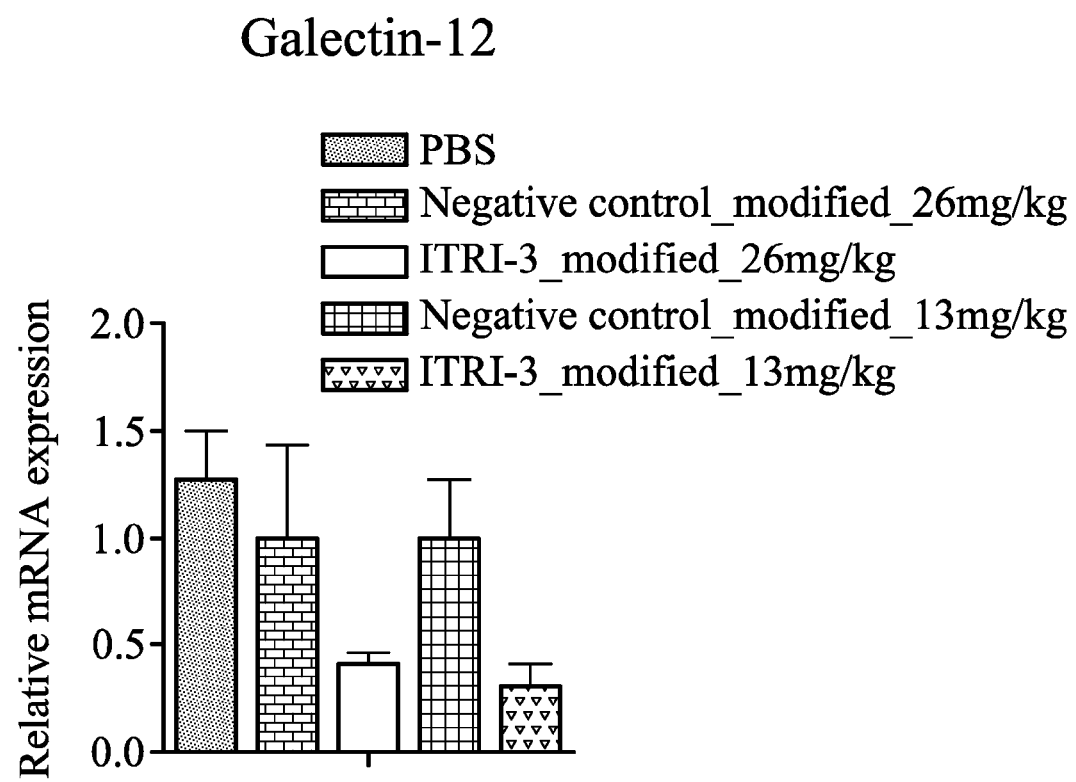
Figure 5A:
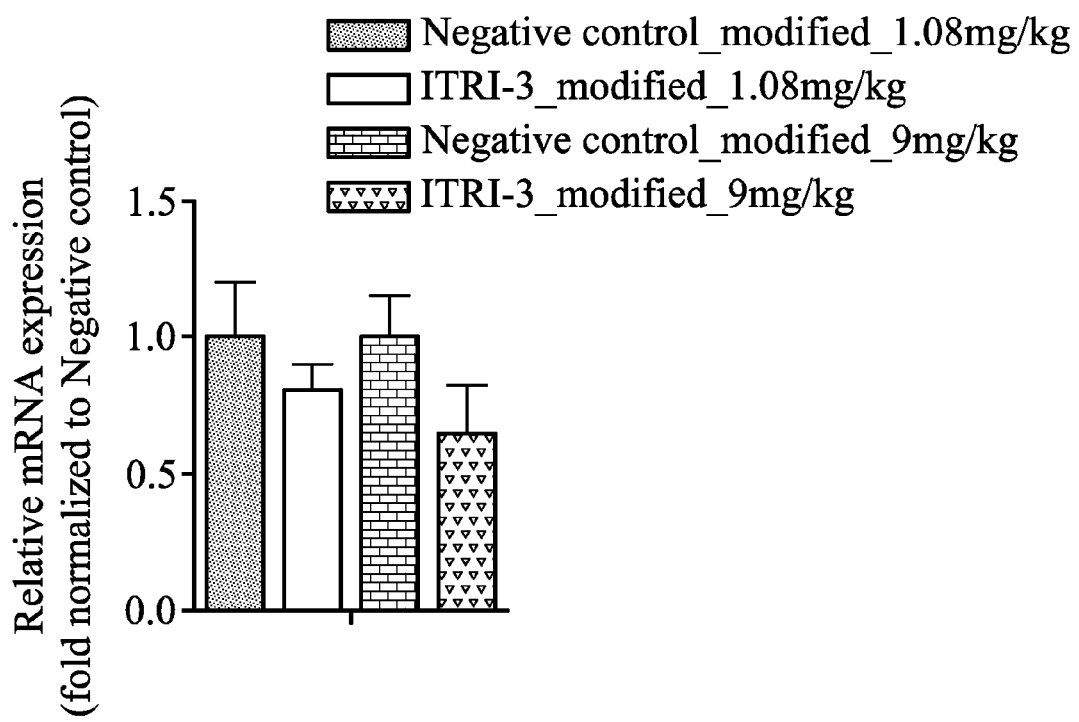
Figure 5B:
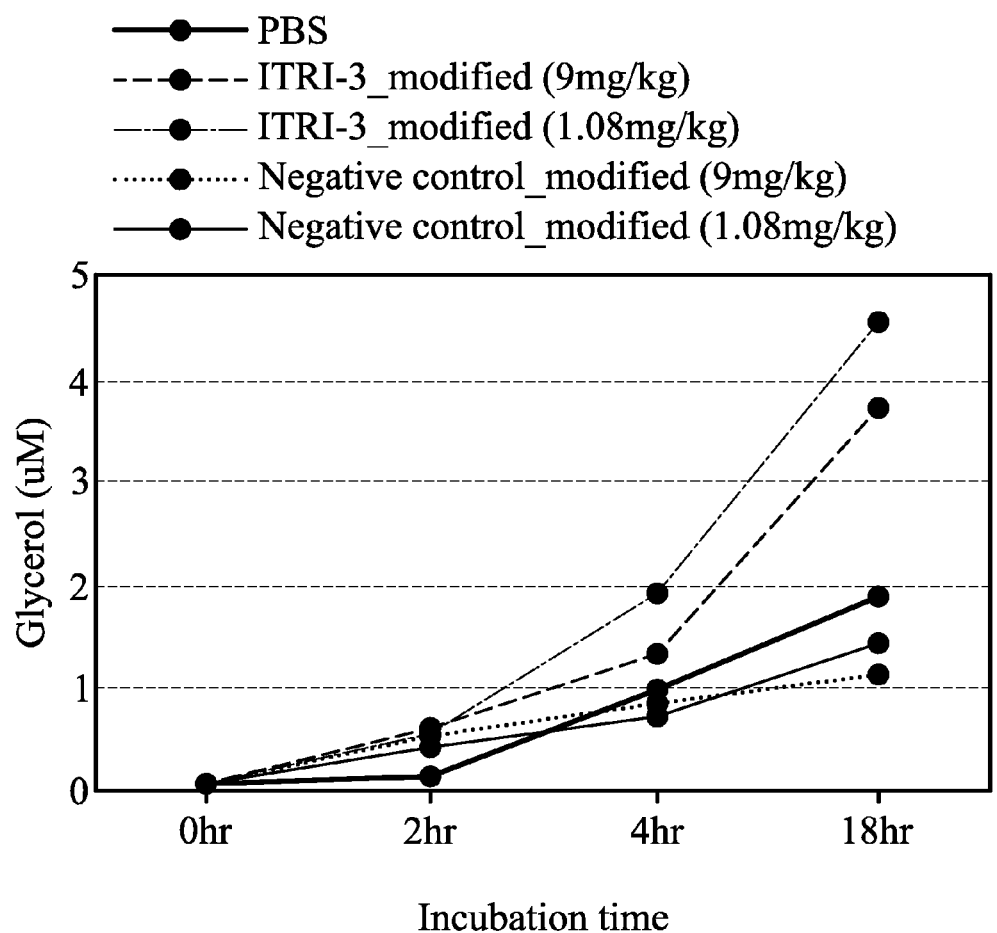
Figure 5C:
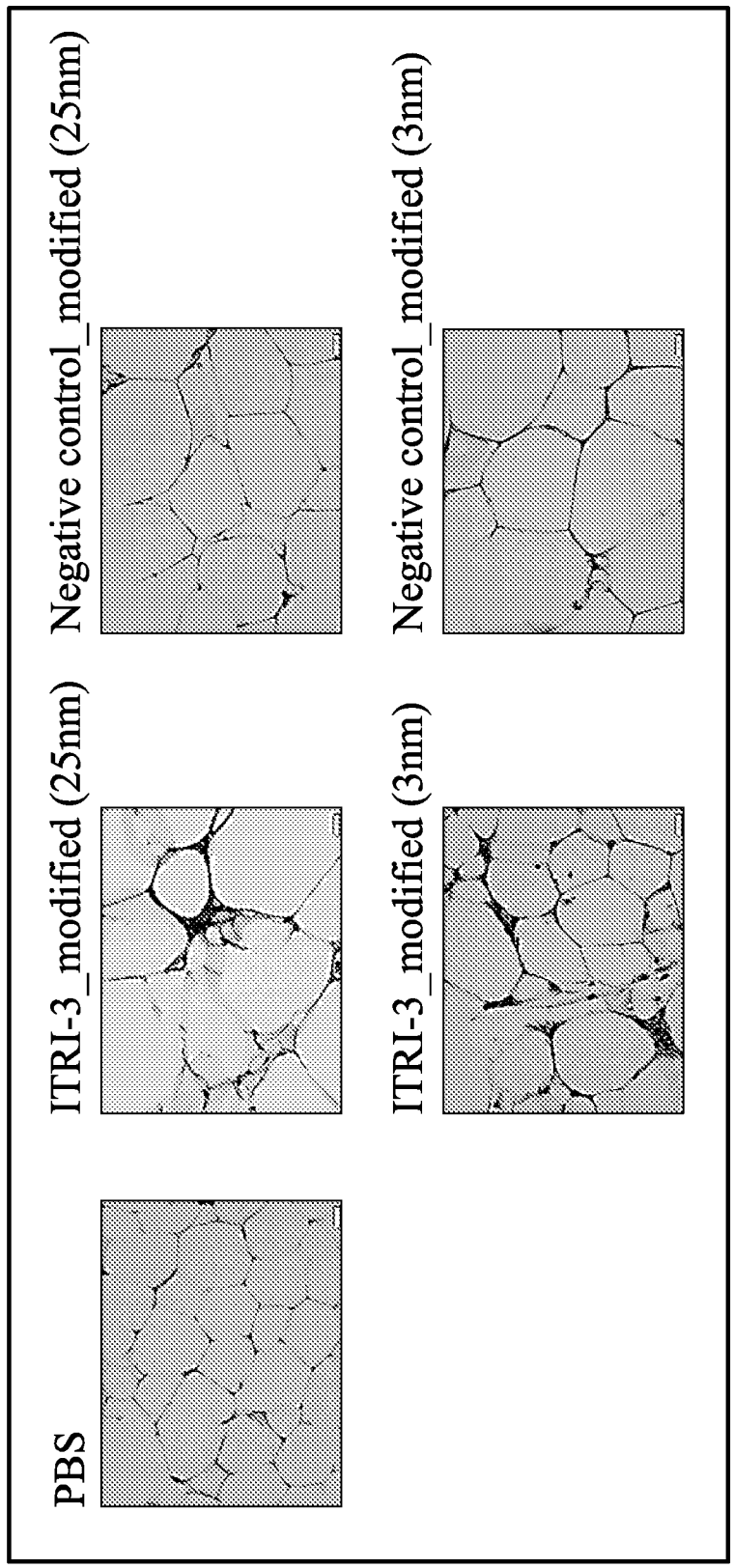

and ITRI-3 galectin-12_siRNA (unmodified form and modified form) according to one embodiment of the present disclosure;

FIG. 2B shows mRNA expression levels of galectin-12 of human mesenchymal stem cell derived adipocytes transfected with negative control siRNA (unmodified form and modified form) and ITRI-3 galectin-12_siRNA (unmodified form and modified form) according to one embodiment of the present disclosure;

FIG. 2C shows mRNA expression levels of galectin-12 of human mesenchymal stem cell derived adipocytes transfected with negative control siRNA (unmodified form) and siRNA-1, ITRI-1, ITRI-2, ITRI-3 galectin-12_siRNAs (unmodified form) according to one embodiment of the present disclosure;

FIG. 3 shows the mRNA expression levels of galectin-12 of the tissue explants (mouse adipose tissue) transfected with negative control siRNA (modified form) and ITRI-3 siRNA (modified form) according to one embodiment of the present disclosure;

FIG. 4 shows the mRNA expression levels of galectin-12 of the adipose tissues of mice receiving PBS buffer, 26 mg/kg negative control siRNA (modified form), 26 mg/kg ITRI-3 galectin-12_siRNA (modified form), 13 mg/kg negative control siRNA (modified form) and 13 mg/kg ITRI-3 galectin-12_siRNA (modified form) according to one embodiment of the present disclosure;

FIG. 5A shows the mRNA expression levels of galectin-12 of the adipose tissues of mice receiving 1.08 mg/kg negative control siRNA (modified form), 1.08 mg/kg ITRI-3 galectin-12_siRNA (modified form), 9 mg/kg negative control siRNA (modified form) and 9 mg/kg ITRI-3 galectin-12_siRNA (modified form) according to one embodiment of the present disclosure;

FIG. 5B shows the lipolysis assay results of the adipose tissues of mice receiving PBS buffer, 1.08 mg/kg negative control siRNA (modified form), 1.08 mg/kg ITRI-3 galectin-12_siRNA (modified form), 9 mg/kg negative control siRNA (modified form) and 9 mg/kg ITRI-3 galectin-12_siRNA (modified form) according to one embodiment of the present disclosure; and FIG. 5C shows the hematoxylin and eosin stains (H&E stains) results of the adipose tissue biopsy of the mice receiving PBS buffer, 1.08 mg/kg negative control siRNA (modified form), 1.08 mg/kg ITRI-3 galectin-12_siRNA (modified form), 9 mg/kg negative control siRNA (modified form) and 9 mg/kg ITRI-3 galectin-12_siRNA (modified form) according to one embodiment of the present disclosure.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

In one embodiment of the present disclosure, the present disclosure provides a small interfering RNA, wherein the small interfering RNA is capable of inhibiting galectin-12 expression and/or enhancing lipolysis. Furthermore, the small interfering RNA of the present disclosure can be used in treatment of disorder related with galectin-12 expression.

Examples of disorder related with galectin-12 expression may comprise metabolic disorder, obesity, etc., but are not limited thereto.

The small interfering RNA mentioned above may comprise (a) a first small interfering RNA consisting of a first passenger strand and a first guide strand, (b) a second small interfering RNA consisting of a second passenger strand and a second guide strand, (c) a third small interfering RNA consisting of a third passenger strand and a third guide strand, or (d) a fourth small interfering RNA consisting of a fourth passenger strand and a fourth guide strand.

Regarding the first small interfering RNA, the sequence of the first passenger strand may be a sequence with at least 85% sequence identity to the sequence of SEQ ID NO. 1, and the sequence of the first guide strand may be a sequence with at least 85% sequence identity to the sequence of SEQ ID NO. 2.

For the first passenger strand, in one embodiment, the sequence of the first passenger strand may be a sequence with at least 85%, such as 85%, 90%, 95%, 98% and 99% sequence identity to the sequence of SEQ ID NO. 1. In another embodiment, the sequence of the first passenger strand may be a sequence with 100% sequence identity to the sequence of SEQ ID NO. 1. In other words, the sequence of the first passenger strand may be the sequence of SEQ ID NO. 1.

In a further embodiment, the sequence of the first passenger strand may be a sequence in which at least one nucleotide of 3'-overhang for enhancing nuclease resistance of a small interfering RNA and/or enhancing RNA-induced silencing complex (RISC) formation is added to the 3' end of the sequence of SEQ ID NO. 1. The at least one nucleotide of 3'-overhang mentioned above may be one, two, three, four or five nucleotides of 3'-overhang, but is not limited thereto. For example, two nucleotides of 3'-overhang, such as two thymine deoxyribonucleotides (dTdT) (DNA), two uracil ribonucleotides (UU) (RNA), one uracil ribonucleotide and one guanine ribonucleotide (UG) (RNA), etc., may be added to the 3' end of the sequence of SEQ ID NO. 1. In a specific embodiment, the sequence of the first passenger strand may be a sequence in which two thymine deoxyribonucleotides (dTdT) (DNA) are added to the 3' end of the sequence of SEQ ID NO. 1, i.e. the sequence of SEQ ID NO. 17.

For the first guide strand, in one embodiment, the sequence of the first guide strand may be a sequence with at least 85%, such as 85%, 90%, 95%, 98% and 99% sequence identity to the sequence of SEQ ID NO. 2. In another embodiment, the sequence of the first guide strand may be a sequence with 100% sequence identity to the sequence of SEQ ID NO. 2. In other words, the sequence of the first guide strand may be the sequence of SEQ ID NO. 2.

In a further embodiment, the sequence of the first guide strand may be a sequence in which at least one nucleotide of 3'-overhang for enhancing nuclease resistance of a small interfering RNA and/or enhancing RNA-induced silencing complex (RISC) formation is added to the 3' end of the sequence of SEQ ID NO. 2. The at least one nucleotide of 3'-overhang mentioned above may be one, two, three, four or five nucleotides of 3'-overhang, but is not limited thereto. For example, two nucleotides of 3'-overhang, such as two thymine deoxyribonucleotides (dTdT) (DNA), two uracil ribonucleotides (UU) (RNA), one uracil ribonucleotide and one guanine ribonucleotide (UG) (RNA), etc., may be added to the 3' end of the sequence of SEQ ID NO. 2. In a specific embodiment, the sequence of the first guide strand may be a sequence in which two thymine deoxyribonucleotides (dTdT) (DNA) are added to the 3' end of the sequence of SEQ ID NO. 2, i.e. the sequence of SEQ ID NO. 18.

In one embodiment, in the first small interfering RNA, the sequence of the first passenger strand may be the sequence of SEQ ID NO. 1, and the sequence of the first guide strand may be the sequence of SEQ ID NO. 2. In another embodiment, in the first small interfering RNA, the sequence of the first passenger strand may be the sequence of SEQ ID NO. 17, and the sequence of the first guide strand may be the sequence of SEQ ID NO. 18.

In another embodiment, the first passenger strand and/or the first guide strand may comprise at least one modified nucleotide and/or at least one modified phosphodiester bond. Examples for the foregoing modified nucleotide may comprise, but are not limited to a 2'-O-methyl nucleotide, 5'-O-methylphosphonate nucleic acid, peptide nucleic acid (PNA), N-Morpholino, locked nucleic acid (LNA), etc. Examples for the foregoing modified phosphodiester bond may comprise a phosphorothioate bond, boranophosphate bond, PNA bond or morpholino bond, but are not limited thereto. In an exemplary embodiment, the foregoing modified nucleotide is a 2'-O-methyl nucleotide and the foregoing modified phosphodiester bond is a phosphorothioate bond.

The first passenger strand and/or the first guide strand of the present disclosure may comprise at least one 2'-O-methyl nucleotide and/or at least one phosphorothioate bond. For example, the first passenger strand and/or the first guide strand of the present disclosure may comprise 1 to 10, 2 to 7 or 3 to 5 2'-O-methyl nucleotides and/or 1 to 10, 2 to 7 or 3 to 5 phosphorothioate bonds.

In this embodiment, the sequence of the first passenger strand may be the sequence shown as SEQ ID NO. 1 in which the nucleotides at position 1, 2, 3, 9 and 12 are further 2'-O-methylated, and the linkages between nucleotides at position 1 and position 2, between nucleotides at position 2 and position 3, between nucleotides at position 3 and position 4, between nucleotides at position 5 and position 6 and between nucleotides at position 17 and position 18 are further modified to phosphorothioate bonds, namely the sequence of SEQ ID NO. 9. In other words, the sequence of SEQ ID NO. 1 after being subjected to the methylations and modifications become the sequence of SEQ ID NO. 9.

Alternately, in this embodiment, the sequence of the first passenger strand may be the sequence shown as SEQ ID NO. 17 in which the nucleotides at position 1, 2, 3, 9 and 12 are further 2'-O-methylated, and the linkages between nucleotides at position 1 and position 2, between nucleotides at position 2 and position 3, between nucleotides at position 3 and position 4, between nucleotides at position 5 and position 6, between nucleotides at position 17 and position 18, between nucleotides at position 19 and position 20 and between nucleotides at position 20 and position 21 are further modified to phosphorothioate bonds, namely the sequence of SEQ ID NO. 25. In other words, the sequence of SEQ ID NO. 17 after being subjected to the methylations and modifications become the sequence of SEQ ID NO. 25.

Also in this embodiment, the sequence of the first guide strand may be the sequence shown as SEQ ID NO. 2 in which the nucleotides at positions 2, 18 and 19 are further 2'-O-methylated, namely the sequence of SEQ ID NO. 10. In other words, the sequence of SEQ ID NO. 2 after being subjected to the methylations become the sequence of SEQ ID NO. 10.

Alternately, in this embodiment, the sequence of the first guide strand may be the sequence shown as SEQ ID NO. 18 in which the nucleotides at positions 2, 18 and 19 are further 2'-O-methylated, and the linkages between nucleotides at position 19 and position 20 and between nucleotides at position 20 and position 21 are further modified to phosphorothioate bonds, namely the sequence of SEQ ID NO. 26. In other words, the sequence of SEQ ID NO. 18 after being subjected to the methylations and modifications become the sequence of SEQ ID NO. 26.

In one embodiment, in the first small interfering RNA, the sequence of the first passenger strand is the sequence of SEQ ID NO. 9, and the sequence of the first guide strand is the sequence of SEQ ID NO. 10. In another embodiment, in the first small interfering RNA, the sequence of the first passenger strand is the sequence of SEQ ID NO. 25, and the sequence of the first guide strand is the sequence of SEQ ID NO. 26.

Moreover, with regard to the second small interfering RNA, the sequence of the second passenger strand may be a sequence with at least 85% sequence identity to the sequence of SEQ ID NO. 3, and the sequence of the second guide strand may be a sequence with at least 85% sequence identity to the sequence of SEQ ID NO. 4.

For the second passenger strand, in one embodiment, the sequence of the second passenger strand may be a sequence with at least 85%, such as 85%, 90%, 95%, 98% and 99% sequence identity to the sequence of SEQ ID NO. 3. In another embodiment, the sequence of the second passenger strand may be a sequence with 100% sequence identity to the sequence of SEQ ID NO. 3. In other words, the sequence of the second passenger strand may be the sequence of SEQ ID NO. 3.

In a further embodiment, the sequence of the second passenger strand may be a sequence in which at least one nucleotide of 3'-overhang for enhancing nuclease resistance of a small interfering RNA and/or enhancing RNA-induced silencing complex (RISC) formation is added to the 3' end of the sequence of SEQ ID NO. 3. The at least one nucleotide of 3'-overhang mentioned above may be one, two, three, four or five nucleotides of 3'-overhang, but is not limited thereto. For example, two nucleotides of 3'-overhang, such as two thymine deoxyribonucleotides (dTdT) (DNA), two uracil ribonucleotides (UU) (RNA), one uracil ribonucleotide and one guanine ribonucleotide (UG) (RNA), etc., may be added to the 3' end of the sequence of SEQ ID NO. 3. In a specific embodiment, the sequence of the second passenger strand may be a sequence in which two thymine deoxyribonucleotides (dTdT) (DNA) are added to the 3' end of the sequence of SEQ ID NO. 3, i.e. the sequence of SEQ ID NO. 19.

For the second guide strand, in one embodiment, the sequence of the second guide strand may be a sequence with at least 85%, such as 85%, 90%, 95%, 98% and 99% sequence identity to the sequence of SEQ ID NO. 4. In another embodiment, the sequence of the second guide strand may be a sequence with 100% sequence identity to the sequence of SEQ ID NO. 4. In other words, the sequence of the second guide strand may be the sequence of SEQ ID NO. 4.

In a further embodiment, the sequence of the second guide strand may be a sequence in which at least one nucleotide of 3'-overhang for enhancing nuclease resistance of a small interfering RNA and/or enhancing RNA-induced silencing complex (RISC) formation is added to the 3' end of the sequence of SEQ ID NO. 4. The at least one nucleotide of 3'-overhang mentioned above may be one, two, three, four or five nucleotides of 3'-overhang, but is not limited thereto. For example, two nucleotides of 3'-overhang, such as two thymine deoxyribonucleotides (dTdT) (DNA), two uracil ribonucleotides (UU) (RNA), one uracil ribonucleotide and one guanine ribonucleotide (UG) (RNA), etc., may be added to the 3' end of the sequence of SEQ ID NO. 4. In a specific embodiment, the sequence of the second guide strand may be a sequence in which two thymine deoxyribonucleotides (dTdT) (DNA) are added to the 3' end of the sequence of SEQ ID NO. 4, i.e. the sequence of SEQ ID NO. 20

In one embodiment, in the second small interfering RNA, the sequence of the second passenger strand may be the sequence of SEQ ID NO. 3, and the sequence of the second guide strand may be the sequence of SEQ ID NO. 4. In another embodiment, in the second small interfering RNA, the sequence of the second passenger strand may be the sequence of SEQ ID NO. 19, and the sequence of the second guide strand may be the sequence of SEQ ID NO. 20.

In another embodiment, the second passenger strand and/or the second guide strand may comprise at least one modified nucleotide and/or at least one modified phosphodiester bond. Examples for the foregoing modified nucleotide may comprise, but are not limited to a 2'-O-methyl nucleotide, 5'-O-methylphosphonate nucleic acid, peptide nucleic acid (PNA), N-Morpholino, locked nucleic acid (LNA), etc. Examples for the foregoing modified phosphodiester bond may comprise a phosphorothioate bond, boranophosphate bond, PNA bond or morpholino bond, but are not limited thereto. In an exemplary embodiment, the foregoing modified nucleotide is a 2'-O-methyl nucleotide and the foregoing modified phosphodiester bond is a phosphorothioate bond.

The second passenger strand and/or the second guide strand of the present disclosure may comprise at least one 2'-O-methyl nucleotide and/or at least one phosphorothioate bond. For example, the second passenger strand and/or the second guide strand of the present disclosure may comprise 1 to 10, 2 to 7 or 3 to 5 2'-O-methyl nucleotides and/or 1 to 10, 2 to 7 or 3 to 5 phosphorothioate bonds.

In this embodiment, the sequence of the second passenger strand may be the sequence shown as SEQ ID NO. 3 in which the nucleotides at position 1, 2, 3, 9 and 12 are further 2'-O-methylated, and the linkages between nucleotides at position 1 and position 2, between nucleotides at position 2 and position 3, between nucleotides at position 3 and position 4, between nucleotides at position 5 and position 6 and between nucleotides at position 17 and position 18 are further modified to phosphorothioate bonds, namely the sequence of SEQ ID NO. 11. In other words, the sequence of SEQ ID NO. 3 after being subjected to the methylations and modifications become the sequence of SEQ ID NO. 11.

Alternately, in this embodiment, the sequence of the second passenger strand may be the sequence shown as SEQ ID NO. 19 in which the nucleotides at position 1, 2, 3, 9 and 12 are further 2'-O-methylated, and the linkages between nucleotides at position 1 and position 2, between nucleotides at position 2 and position 3, between nucleotides at position 3 and position 4, between nucleotides at position 5 and position 6, between nucleotides at position 17 and position 18, between nucleotides at position 19 and position 20 and between nucleotides at position 20 and position 21 are further modified to phosphorothioate bonds, namely the sequence of SEQ ID NO. 27. In other words, the sequence of SEQ ID NO. 19 after being subjected to the methylations and modifications become the sequence of SEQ ID NO. 27.

Also in this embodiment, the sequence of the second passenger strand may be the sequence shown as SEQ ID NO. 4 in which the nucleotides at positions 2, 18 and 19 are further 2'-O-methylated, namely the sequence of SEQ ID NO. 12. In other words, the sequence of SEQ ID NO. 4 after being subjected to the methylations become the sequence of SEQ ID NO. 12.

Alternately, in this embodiment, the sequence of the second guide strand may be the sequence shown as SEQ ID NO. 20 in which the nucleotides at positions 2, 18 and 19 are further 2'-O-methylated, and the linkages between nucleotides at position 19 and position 20 and between nucleotides at position 20 and position 21 are further modified to phosphorothioate bonds, namely the sequence of SEQ ID NO. 28. In other words, the sequence of SEQ ID NO. 20 after being subjected to the methylations and modifications become the sequence of SEQ ID NO. 28.

In one embodiment, in the second small interfering RNA, the sequence of the second passenger strand may be the sequence of SEQ ID NO. 11, and the sequence of the second guide strand may be the sequence of SEQ ID NO. 12. In another embodiment, in the second small interfering RNA, the sequence of the second passenger strand may be the sequence of SEQ ID NO. 27, and the sequence of the second guide strand may be the sequence of SEQ ID NO. 28.

Furthermore, concerning the third small interfering RNA, the sequence of the third passenger strand may be a sequence with at least 85% sequence identity to the sequence of SEQ ID NO. 5, and the sequence of the third guide strand may be a sequence with at least 85% sequence identity to the sequence of SEQ ID NO. 6.

For the third passenger strand, in one embodiment, the sequence of the third passenger strand may be a sequence with at least 85%, such as 85%, 90%, 95%, 98% and 99% sequence identity to the sequence of SEQ ID NO. 5. In another embodiment, the sequence of the third passenger strand may be a sequence with 100% sequence identity to the sequence of SEQ ID NO. 5. In other words, the sequence of the third passenger strand may be the sequence of SEQ ID NO. 5.

In a further embodiment, the sequence of the third passenger strand may be a sequence in which at least one nucleotide of 3'-overhang for enhancing nuclease resistance of a small interfering RNA and/or enhancing RNA-induced silencing complex (RISC) formation is added to the 3' end of the sequence of SEQ ID NO. 5. The at least one nucleotide of 3'-overhang mentioned above may be one, two, three, four or five nucleotides of 3'-overhang, but is not limited thereto. For example, two nucleotides of 3'-overhang, such as two thymine deoxyribonucleotides (dTdT) (DNA), two uracil ribonucleotides (UU) (RNA), one uracil ribonucleotide and one guanine ribonucleotide (UG) (RNA), etc., may be added to the 3' end of the sequence of SEQ ID NO. 5. In a specific embodiment, the sequence of the third passenger strand may be a sequence in which two thymine deoxyribonucleotides (dTdT) (DNA) are added to the 3' end of the sequence of SEQ ID NO. 5, i.e. the sequence of SEQ ID NO. 21.

For the third guide strand, in one embodiment, the sequence of the third guide strand may be a sequence with at least 85%, such as 85%, 90%, 95%, 98% and 99% sequence identity to the sequence of SEQ ID NO. 6. In another embodiment, the sequence of the third guide strand may be a sequence with 100% sequence identity to the sequence of SEQ ID NO. 6. In other words, the sequence of the third guide strand may be the sequence of SEQ ID NO. 6.

In a further embodiment, the sequence of the third guide strand may be a sequence in which at least one nucleotide of 3'-overhang for enhancing nuclease resistance of a small interfering RNA and/or enhancing RNA-induced silencing complex (RISC) formation is added to the 3' end of the sequence of SEQ ID NO. 6. The at least one nucleotide of 3'-overhang mentioned above may be one, two, three, four or five nucleotides of 3'-overhang, but is not limited thereto. For example, two nucleotides of 3'-overhang, such as two thymine deoxyribonucleotides (dTdT) (DNA), two uracil ribonucleotides (UU) (RNA), one uracil ribonucleotide and one guanine ribonucleotide (UG) (RNA), etc., may be added to the 3' end of the sequence of SEQ ID NO. 6. In a specific embodiment, the sequence of the third guide strand may be a sequence in which two thymine deoxyribonucleotides (dTdT) (DNA) are added to the 3' end of the sequence of SEQ ID NO. 6, i.e. the sequence of SEQ ID NO. 22.

In one embodiment, in the third small interfering RNA, the sequence of the third passenger strand may be the sequence of SEQ ID NO. 5, and the sequence of the third guide strand may be the sequence of SEQ ID NO. 6. In another embodiment, in the third small interfering RNA, the sequence of the third passenger strand may be the sequence of SEQ ID NO. 21, and the sequence of the third guide strand may be the sequence of SEQ ID NO. 22.

In another embodiment, the third passenger strand and/or the third guide strand may comprise at least one modified nucleotide and/or at least one modified phosphodiester bond. Examples for the foregoing modified nucleotide may comprise, but are not limited to a 2'-O-methyl nucleotide, 5'-O-methylphosphonate nucleic acid, peptide nucleic acid (PNA), N-Morpholino, locked nucleic acid (LNA), etc. Examples for the foregoing modified phosphodiester bond may comprise a phosphorothioate bond, boranophosphate bond, PNA bond or morpholino bond, but are not limited thereto. In an exemplary embodiment, the foregoing modified nucleotide is a 2'-O-methyl nucleotide and the foregoing modified phosphodiester bond is a phosphorothioate bond.

The third passenger strand and/or the third guide strand of the present disclosure may comprise at least one 2'-O-methyl nucleotide and/or at least one phosphorothioate bond. For example, the third passenger strand and/or the third guide strand of the present disclosure may comprise 1 to 10, 2 to 7 or 3 to 5 2'-O-methyl nucleotides and/or 1 to 10, 2 to 7 or 3 to 5 phosphorothioate bonds.

In this embodiment, the sequence of the third passenger strand may be the sequence shown as SEQ ID NO. 5 in which the nucleotides at position 1, 2, 3, 9 and 12 are further 2'-O-methylated, and the linkages between nucleotides at position 1 and position 2, between nucleotides at position 2 and position 3, between nucleotides at position 3 and position 4, between nucleotides at position 5 and position 6 and between nucleotides at position 17 and position 18 are further modified to phosphorothioate bonds, namely the sequence of SEQ ID NO. 13. In other words, the sequence of SEQ ID NO. 5 after being subjected to the methylations and modifications become the sequence of SEQ ID NO. 13.

Alternately, in this embodiment, the sequence of the third passenger strand may be the sequence shown as SEQ ID NO. 21 in which the nucleotides at position 1, 2, 3, 9 and 12 are further 2'-O-methylated, and the linkages between nucleotides at position 1 and position 2, between nucleotides at position 2 and position 3, between nucleotides at position 3 and position 4, between nucleotides at position 5 and position 6, between nucleotides at position 17 and position 18, between nucleotides at position 19 and position 20 and between nucleotides at position 20 and position 21 are further modified to phosphorothioate bonds, namely the sequence of SEQ ID NO. 29. In other words, the sequence of SEQ ID NO. 21 after being subjected to the methylations and modifications become the sequence of SEQ ID NO. 29.

Also in this embodiment, the sequence of the third passenger strand may be the sequence shown as SEQ ID NO. 6 in which the nucleotides at positions 2, 18 and 19 are further 2'-O-methylated, namely the sequence of SEQ ID NO. 14. In other words, the sequence of SEQ ID NO. 6 after being subjected to the methylations become the sequence of SEQ ID NO. 14.

Alternately, in this embodiment, the sequence of the third guide strand may be the sequence shown as SEQ ID NO. 22 in which the nucleotides at positions 2, 18 and 19 are further 2'-O-methylated, and the linkages between nucleotides at position 19 and position 20 and between nucleotides at position 20 and position 21 are further modified to phosphorothioate bonds, namely the sequence of SEQ ID NO. 30. In other words, the sequence of SEQ ID NO. 22 after being subjected to the methylations and modifications become the sequence of SEQ ID NO. 30.

In one embodiment, in the third small interfering RNA, the sequence of the third passenger strand may be the sequence of SEQ ID NO. 13, and the sequence of the third guide strand may be the sequence of SEQ ID NO. 14. In another embodiment, in the thirdsmall interfering RNA, the sequence of the second passenger strand may be the sequence of SEQ ID NO. 29, and the sequence of the second guide strand may be the sequence of SEQ ID NO. 30.

In addition, regarding the fourth small interfering RNA, the sequence of the fourth passenger strand may be a sequence with at least 85% sequence identity to the sequence of SEQ ID NO. 7, and the sequence of the fourth guide strand may be a sequence with at least 85% sequence identity to the sequence of SEQ ID NO. 8.

For the fourth passenger strand, in one embodiment, the sequence of the fourth passenger strand may be a sequence with at least 85%, such as 85%, 90%, 95%, 98% and 99% sequence identity to the sequence of SEQ ID NO. 7. In another embodiment, the sequence of the fourth passenger strand may be a sequence with 100% sequence identity to the sequence of SEQ ID NO. 7. In other words, the sequence of the fourth passenger strand may be the sequence of SEQ ID NO. 7.

In a further embodiment, the sequence of the fourth passenger strand may be a sequence in which at least one nucleotide of 3'-overhang for enhancing nuclease resistance of a small interfering RNA and/or enhancing RNA-induced silencing complex (RISC) formation is added to the 3' end of the sequence of SEQ ID NO. 7. The at least one nucleotide of 3'-overhang mentioned above may be one, two, three, four or five nucleotides of 3'-overhang, but is not limited thereto. For example, two nucleotides of 3'-overhang, such as two thymine deoxyribonucleotides (dTdT) (DNA), two uracil ribonucleotides (UU) (RNA), one uracil ribonucleotide and one guanine ribonucleotide (UG) (RNA), etc., may be added to the 3' end of the sequence of SEQ ID NO. 7. In a specific embodiment, the sequence of the fourth passenger strand may be a sequence in which two thymine deoxyribonucleotides (dTdT) (DNA) are added to the 3' end of the sequence of SEQ ID NO. 7, i.e. the sequence of SEQ ID NO. 23.

For the fourth guide strand, in one embodiment, the sequence of the fourth guide strand may be a sequence with at least 85%, such as 85%, 90%, 95%, 98% and 99% sequence identity to the sequence of SEQ ID NO. 8. In another embodiment, the sequence of the fourth guide strand may be a sequence with 100% sequence identity to the sequence of SEQ ID NO. 8. In other words, the sequence of the fourth guide strand may be the sequence of SEQ ID NO. 8.

In a further embodiment, the sequence of the fourth guide strand may be a sequence in which at least one nucleotide of 3'-overhang for enhancing nuclease resistance of a small interfering RNA and/or enhancing RNA-induced silencing complex (RISC) formation is added to the 3' end of the sequence of SEQ ID NO. 8. The at least one nucleotide of 3'-overhang mentioned above may be one, two, three, four or five nucleotides of 3'-overhang, but is not limited thereto. For example, two nucleotides of 3'-overhang, such as two thymine deoxyribonucleotides (dTdT) (DNA), two uracil ribonucleotides (UU) (RNA), one uracil ribonucleotide and one guanine ribonucleotide (UG) (RNA), etc., may be added to the 3' end of the sequence of SEQ ID NO. 8. In a specific embodiment, the sequence of the fourth guide strand may be a sequence in which two thymine deoxyribonucleotides (dTdT) (DNA) are added to the 3' end of the sequence of SEQ ID NO. 8, i.e. the sequence of SEQ ID NO. 24.

In one embodiment, in the fourth small interfering RNA, the sequence of the fourth passenger strand may be the sequence of SEQ ID NO. 7, and the sequence of the fourth guide strand may be the sequence of SEQ ID NO. 8. In another embodiment, in the fourth small interfering RNA, the sequence of the fourth passenger strand may be the sequence of SEQ ID NO. 23, and the sequence of the fourth guide strand may be the sequence of SEQ ID NO. 24.

In another embodiment, the fourth passenger strand and/or the fourth guide strand may comprise at least one modified nucleotide and/or at least one modified phosphodiester bond. Examples for the foregoing modified nucleotide may comprise, but are not limited to a 2'-O-methyl nucleotide, 5'-O-methylphosphonate nucleic acid, peptide nucleic acid (PNA), N-Morpholino, locked nucleic acid (LNA), etc. Examples for the foregoing modified phosphodiester bond may comprise a phosphorothioate bond, boranophosphate bond, PNA bond or morpholino bond, but are not limited thereto. In an exemplary embodiment, the foregoing modified nucleotide is a 2'-O-methyl nucleotide and the foregoing modified phosphodiester bond is a phosphorothioate bond.

The fourth passenger strand and/or the fourth guide strand of the present disclosure may comprise at least one 2'-O-methyl nucleotide and/or at least one phosphorothioate bond. For example, the fourth passenger strand and/or the fourth guide strand of the present disclosure may comprise 1 to 10, 2 to 7 or 3 to 5 2'-O-methyl nucleotides and/or 1 to 10, 2 to 7 or 3 to 5 phosphorothioate bonds.

In this embodiment, the sequence of the fourth passenger strand may be the sequence shown as SEQ ID NO. 7 in which the nucleotides at position 1, 2, 3, 9 and 12 are further 2'-O-methylated, and the linkages between nucleotides at position 1 and position 2, between nucleotides at position 2 and position 3, between nucleotides at position 3 and position 4, between nucleotides at position 5 and position 6 and between nucleotides at position 17 and position 18 are further modified to phosphorothioate bonds, namely the sequence of SEQ ID NO. 15. In other words, the sequence of SEQ ID NO. 7 after being subjected to the methylations and modifications become the sequence of SEQ ID NO. 15.

Alternately, in this embodiment, the sequence of the fourth passenger strand may be the sequence shown as SEQ ID NO. 23 in which the nucleotides at position 1, 2, 3, 9 and 12 are further 2'-O-methylated, and the linkages between nucleotides at position 1 and position 2, between nucleotides at position 2 and position 3, between nucleotides at position 3 and position 4, between nucleotides at position 5 and position 6, between nucleotides at position 17 and position 18, between nucleotides at position 19 and position 20 and between nucleotides at position 20 and position 21 are further modified to phosphorothioate bonds, namely the sequence of SEQ ID NO. 31. In other words, the sequence of SEQ ID NO. 23 after being subjected to the methylations and modifications become the sequence of SEQ ID NO. 31.

Also in this embodiment, the sequence of the fourth passenger strand may be the sequence shown as SEQ ID NO. 8 in which the nucleotides at positions 2, 18 and 19 are further 2'-O-methylated, namely the sequence of SEQ ID NO. 16. In other words, the sequence of SEQ ID NO. 8 after being subjected to the methylations become the sequence of SEQ ID NO. 16.

Alternately, in this embodiment, the sequence of the fourth guide strand may be the sequence shown as SEQ ID NO. 24 in which the nucleotides at positions 2, 18 and 19 are further 2'-O-methylated, and the linkages between nucleotides at position 19 and position 20 and between nucleotides at position 20 and position 21 are further modified to phosphorothioate bonds, namely the sequence of SEQ ID NO. 32. In other words, the sequence of SEQ ID NO. 24 after being subjected to the methylations and modifications become the sequence of SEQ ID NO. 32.

In one embodiment, in the fourth small interfering RNA, the sequence of the fourth passenger strand may be the sequence of SEQ ID NO. 15, and the sequence of the fourth guide strand may be the sequence of SEQ ID NO. 16. In another embodiment, in the fourth small interfering RNA, the sequence of the second passenger strand may be the sequence of SEQ ID NO. 31, and the sequence of the second guide strand may be the sequence of SEQ ID NO. 32.

Moreover, any preceding small interfering RNA of the present disclosure can be formulated in to a medicament alone or with a pharmaceutically acceptable carrier or salt.

The pharmaceutically acceptable carrier mentioned above may comprise, but is not limited to, a liposome, a micelle, a metal particle, a polymer particle, a solvent, a dispersion medium, a coating, an antibacterial and antifungal agent, or an isotonic, absorption delaying agent, etc. which is compatible to pharmaceutical administration. The pharmaceutical composition can be formulated into dosage forms for different administration routes utilizing conventional methods. In one embodiment, the pharmaceutically acceptable carrier mentioned above may be a liposome, a micelle, a metal particle or a polymer particle.

Particles mentioned above can be prepared from a variety of materials such as lipids, proteins, polysaccharides and synthetic polymers. Depending upon the method of preparation, nanoparticles, nanospheres or nanocapsules can be obtained.

Furthermore, the pharmaceutically acceptable salt mentioned above may comprise, but is not limited to, inorganic cation salt, such as alkali metal salts such as sodium salt, potassium salt or amine salt, such as alkaline-earth metal salt such as magnesium salt or calcium salt, such as the salt containing bivalent or quadrivalent cation such as zinc salt, aluminum salt or zirconium salt. In addition, the pharmaceutically acceptable salt may also comprise organic salt, such as dicyclohexylamine salt, methyl-D-glucamine, and amino acid salt such as arginine, lysine, histidine, or glutamine.

In another embodiment of the present disclosure, the present disclosure provides a pharmaceutical composition for inhibiting galectin-12 expression and/or enhancing lipolysis. The pharmaceutical composition for inhibiting galectin-12 expression and/or enhancing lipolysis may comprise any small interfering RNA of the present disclosure mentioned above, but is not limited thereto.

In one embodiment, the pharmaceutical composition for inhibiting galectin-12 expression and/or enhancing lipolysis may further comprise a pharmaceutically acceptable carrier or salt.

Description for the pharmaceutically acceptable carrier contained by the pharmaceutical composition of the present disclosure may be referred to above. In one embodiment, the pharmaceutically acceptable carrier mentioned above may be a liposome, a micelle, a metal particle or a polymer particle.

Moreover, description for the pharmaceutically acceptable salt contained by the pharmaceutical composition of the present disclosure may be also referred to above.

The pharmaceutical composition of the present disclosure may be administered orally, parenterally by an inhalation spray, or via an implanted reservoir. The parenteral method may comprise subcutaneous, intracutaneous, intravenous, intramuscular, intra-articular, intra-arterial, intrasynovial, intrasternal, intrathecal, and intraleaional, as well as infusion techniques.

An oral composition can comprise, but is not limited to, tablets, capsules, emulsions, and aqueous suspensions, dispersions and solutions.

In another embodiment of the present disclosure, the present disclosure provides a method for inhibiting galectin-12 expression and/or enhancing lipolysis. The method for inhibiting galectin-12 expression and/or enhancing lipolysis of the present disclosure can also be considered as a method for treating a disorder related with galectin-12 expression. Examples of disorder related with galectin-12 expression may comprise metabolic disorder, obesity, etc., but are not limited thereto.

The method for inhibiting galectin-12 expression and/or enhancing lipolysis of the present application may comprise, but is not limited to administering an effective amount of any foregoing pharmaceutical composition of the present disclosure mentioned above to a subject in need.

The subject may be a mammal, such as mouse, rat, guinea pig, rabbit, dog, cat, monkey, orangutan, human, etc., but is not limited thereto. In one embodiment, the subject may be a human.

In one embodiment, the subject in need may suffer from treating a disorder related with galectin-12 expression, such as obesity.

EXAMPLES

A. Material and Methods 1. siRNA Design and Modifications

A set of siRNAs were designed to target galectin-12 mRNA and its variants in human or mouse species. The sequences constitutions, targets and modifications were summarized in Table 1. siRNA-1, ITRI-1 and ITRI-2 (unmodified form and modified form) were designed for human galectin-12 mRNA silencing. For animal study requirement in further drug development, a specific siRNA, ITRI-3 (unmodified form and modified form), that could target to human and mouse galectin-12 mRNA and its variants was also designed. The chemical modifications of the siRNA, including backbone phosphorothioate and sugar 2'-OMe, are suggested to reduce induced innate immune responses, decrease off-target effects, and increase serum stability.

TABLE 1

| ID | Modification form | Strand | Sequence (5' to 3') | siRNA target |
|---|---|---|---|---|
| siRNA-1 | Unmodified form | Passenger strand | UGGGCAGGUCAUCAUAGUATT (SEQ ID NO. 17) | Homo sapiens lectin, galactoside-binding, |
|  |  | Guide strand | UACUAUGAUGACCUGCCCATT (SEQ ID NO. 18) | soluble 12 (LGALS12), mRNA: |
|  | Modified form | Passenger strand | U*G*G*GC*AGGUCAUCAUAG*UA*T*T (SEQ ID NO. 25) | (NM_001142535, M_033101, |
|  |  | Guide strand | UACUAUGAUGACCUGCCCA*T*T (SEQ ID NO. 26) | NM_001142536, NM_001142537, NM_001142538) |
| ITRI-1 | Unmodified form | Passenger strand | GUGGUUCCUUAUGUCACGATT (SEQ ID NO. 19) | Homo sapiens lectin, galactoside-binding, |
|  |  | Guide strand | UCGUGACAUAAGGAACCACTT (SEQ ID NO. 20) | soluble, 12 (LGALS12), mRNA: |
|  | Modified form | Passenger strand | G*U*G*GU*UCCUUAUGUCAC*GA*T*T (SEQ ID NO. 27) | (NM_001142535, M_033101, |
|  |  | Guide strand | UCGUGACAUAAGGAACCAC*T*T (SEQ ID NO. 28) | NM_001142536, NM_001142537, NM_001142538) |
| ITRI-2 | Unmodified form | Passenger strand | GGGCAGAAGAAACUGAUCUTT (SEQ ID NO. 21) | Homo sapiens lectin, galactoside-binding, |
|  |  | Guide strand | AGAUCAGUUUCUUCUGCCCTT (SEQ ID NO. 22) | soluble 12 (LGALS12), mRNA: |
|  | Modified form | Passenger strand | G*G*G*CA*GAAGAAACUGAU*CU*T*T (SEQ ID NO. 29) | (NM_001142535, M_033101, |
|  |  | Guide strand | AGAUCAGUUUCUUCUGCCC*T*T (SEQ ID NO. 30) | NM_001142536, NM_001142537, NM_001142538) |
| ITRI-3 | Unmodified form | Passenger strand | CUGUUGGAUUCCUGAACAUTT (SEQ ID NO. 23) | Homo sapiens lectin, galactoside-binding, |
|  |  | Guide strand | AUGUUCAGGAAUCCAACAGTT (SEQ ID NO. 24) | soluble, 12 (LGALS12), mRNA: |
|  | Modified form | Passenger strand | C*U*G*UU*GGAUUCCUGAAC*AU*T*T (SEQ ID NO. 31) | (NM_001142535, M_033101, |

TABLE 1-continued

| ID | Modification form | Strand | Sequence (5' to 3') | siRNA target |
|---|---|---|---|---|
| | | Guide strand | A<u>U</u>GUUCAGGAAUCCAAC<u>AG</u>*T*T (SEQ ID NO. 32) | NM_001142536, NM_001142537, NM_001142538); *Mus musculus* lectin, galactoside-binding, soluble 12 (Lgals12), mRNA: (NM_019516, XM_006527219, XM_006527220, XM_006527221 |
| Negative control siRNA | Unmodified form | Passenger strand | UAAGGCUAUGAAGAGAUACTT (SEQ ID NO. 33) | |
| | | Guide strand | GUAUCUCUUCAUAGCCUUATT (SEQ ID NO. 34) | |
| | Modified form | Passenger strand | U*<u>A</u>*<u>A</u>*GG*CU<u>A</u>UG<u>AA</u>GAGAU*AC*T*T (SEQ ID NO. 35) | |
| | | Guide strand | G<u>U</u>AUCUCUUCAUAGCCU<u>UA</u>*T*T (SEQ ID NO. 36) | |

Modification Notes:
Nucleotide marked with under line: 2'-O-methylation;
*phosphorothioate bond.
T: thymine deoxyribonucleotide (dT)

2. Effects of Chemical Modification for siRNAs

Serum Stability Test

Unmodified and modified siRNAs (1 uM) were incubated at 37° C. in 50% serum of different species (human, mouse or fetal bovine serums). Sampling aliquots of 5 μl were collected at different time points (0 hour, 1 hour, 6 hours, 24 hours, 48 hours or 72 hours) and immediately storage at −20° C. Collected siRNA sample was electrophoresed in 2% agarose gels at 1×TAE buffer under 100V for 20 minutes, and then the gels were stained with SYBR gold for 30 minutes with gentle rocking and then photographed immediately. Using a SYBR Green photographic condition (Excitation maxima for dye-nucleic acid complexes are at ~495 nm and ~300 nm and the emission maximum is ~537 nm), stained gel image was visualized and captured by ImageQuant LAS 4000 (GE Healthcare Life Sciences).

3. Cell Cultures (1) Human Mesenchymal Stem Cells

Human mesenchymal stem cells were cultured in α-MEM (Gibco), 10% fetal bovine serum, 2 mM L-glutamin (Gibco), 100 U/ml penicillin+100 mg/ml streptomycin (Gibco) and 1 ng/ml bFGF (Instruchemie, PhP105) in a humidified atmosphere containing 5% $CO_2$ at 37° C.

(2) NIH-3T3-L1 Cells

NIH-3T3-L1 cells were cultured in DMEM (Gibco), 100 U/ml penicillin+100 mg/ml streptomycin (Gibco), and 10% fetal bovine serum.

4. Induction of Adipocyte Differentiation (1) Human Mesenchymal Stem Cells

To induce differentiation, confluent cells will be exposed to a pro-differentiative regimen consisting of DMEM (Gibco), 100 U/ml penicillin+100 mg/ml streptomycin (Gibco), 10% fetal bovine serum, 0.2 mM Indomethacin (Sigma), 0.5 mM IBMX (Sigma), $10^{-6}$ M dexamethasone (Sigma), 10 mg/ml Insulin (human, Sigma) in culture medium for 2 days. The cells will be subsequently cultured in medium with insulin only.

(2) NIH-3T3-L1 Cells

To induce differentiation, confluent cells will be exposed to a pro-differentiative regimen consisting of DMEM (Gibco), 100 U/ml penicillin+100 mg/ml streptomycin (Gibco), 10% fetal bovine serum, 0.2 mM Indomethacin (Sigma), 0.5 mM IBMX (Sigma), $10^{-6}$ M dexamethasone (Sigma), 10 mg/ml Insulin (human, Sigma) in culture medium for 2 days. The cells will be subsequently cultured in medium with insulin only.

5. siRNA Transfection in NIH-3T3-L1 Cells and Human Mesenchymal Stem Cell Derived Adipocytes (Knock Down of Galectin-12 in Induced Differentiated Adipocytes)

(1) siRNA Transfection in NIH-3T3-L1 Cells Cell Derived Adipocytes 150 nM of negative control siRNA (unmodified form and modified form) and ITRI-3 galectin-12_siRNA (unmodified form and modified form) were delivered into differentiated adipocytes by commercial siRNA transfection reagent (INTERFERin®; Polyplus Transfection). By following the manufacturer's protocol, for 48 hours transfection, RNA sample were collected and extracted from the cells. A specific TaqMan® quantitative polymerase chain reaction (qPCR) assay was conducted to examine the mRNA expression level of galectin-12.

(2) siRNA Transfection in Human Mesenchymal Stem Cell Derived Adipocytes (i) ITRI-3 Galectin-12_siRNA (Unmodified Form and Modified Form)

130 and 170 nM of negative control siRNA (unmodified form and modified form) and ITRI-3 galectin-12_siRNA (unmodified form and modified form) were delivered into differentiated adipocytes by commercial siRNA transfection reagent (INTERFERin®; Polyplus Transfection). By following the manufacturer's protocol, for 48 hours transfection, RNA sample were collected and extracted from the cells. A specific qPCR assay was conducted to examine the mRNA expression level of galectin-12.

(ii) siRNA-1, ITRI-1, ITRI-2 and ITRI-3 Galectin-12_siRNAs (Unmodified Form)

150 nM of negative control siRNA (unmodified form) and siRNA-1, ITRI-1, ITRI-2, ITRI-3 galectin-12_siRNAs (unmodified form) were delivered into differentiated adipocytes by commercial siRNA transfection reagent (INTERFERin®; Polyplus Transfection). By following the manufacturer's protocol, for 48 hours transfection, RNA sample were collected and extracted from the cells. A specific qPCR assay was conducted to examine the mRNA expression level of galectin-12.

6. Transfection of siRNAs in Primary Tissue (Ex Vivo Knock Down Galectin-12 in Mouse Adipose Tissue)

Epididymal fat pads were obtained from 10-week-old male C57 BL/6J mice. Freshly procured adipose tissue was washed with PBS under sterile conditions. For each transfection, 60-80 mg of tissue was minced to a size of approximately 1-2 mm. The tissue explants were resuspended in 200 μl electroporation buffer mixed with 16 nmol negative control siRNA (modified form) or ITRI-3 siRNA (modified form) in an electroporation cuvette (0.4 cm) and subjected to sixteen shocks of 50 V or 80 V with a time constant of 30 msec on a BTX electroporator Immediately after electroporation, DMEM supplemented with 10% fetal bovine serum, 100 U/ml penicillin+100 mg/ml streptomycin was added, and the explants were incubated at 37° C. in 5% $CO_2$. The medium was changed after 2 hours, then after 5 hours, and thereafter every 24 hours for 48 hours. RNA was extracted from the tissues and qPCR analysis was conducted to examine the mRNA expression level of galectin-12 of the tissues.

7. siRNA Studies In Vivo (In Vivo Knockdown Galectin-12 in Mouse Adipose Tissue)

Fifteen 10-week-old male mice were randomly assigned to 5 groups receiving PBS buffer (n=3), 26 mg/kg negative control siRNA (modified form) (n=3), 26 mg/kg ITRI-3 galectin-12_siRNA (modified form) (n=3), 13 mg/kg negative control siRNA (modified form) (n=3) and 13 mg/kg ITRI-3 galectin-12_siRNA (modified form) (n=3). Mice were injected using intravenous injection (i.v.) or intraperitoneal injection (i.p.) with PBS buffer or siRNAs (26 mg/kg or 13 mg/kg) every 3 days for 2 weeks. RNA was extracted from the tissue and qPCR analysis was conducted to examine the mRNA expression level of galectin-12.

8. siRNA Studies In Vivo (In Vivo Knockdown Galectin-12 Induces Lipolysis of Mouse Adipose Tissue in Obesity Animal Mode)

(1) Treatment for Animals

Twenty 6-week-old male mice were fattened with high-fat diet feeding stuff for eight weeks to increase the body weight to about 40 g, and then randomly assigned to 4 groups receiving 1.08 mg/kg negative control siRNA (modified form) (n=5), 1.08 mg/kg ITRI-3 galectin-12_siRNA (modified form) (n=5), 9 mg/kg negative control siRNA (modified form) (n=5) and 9 mg/kg ITRI-3 galectin-12_siRNA (modified form) (n=5). In addition, five 14-week-old male mice which were not fattened with high-fat diet feeding (n=5) were assigned to a PBS receiving buffer group as a negative control group. Mice were injected using intravenous injection (i.v.) or intraperitoneal injection (i.p.) with PBS buffer or siRNAs (10.8 mg/kg or 9 mg/kg) twice a week for 42 days.

(2) mRNA Expression Level of Galectin-12

RNA was extracted from the adipose tissue of the mice of each group mentioned above and qPCR analysis was conducted to examine the mRNA expression level of galectin-12.

(3) Lipolysis Assay

Lipolysis in the adipocytes of the mice of each group mentioned above was monitored by measuring fatty acid and glycerol release. Briefly, adipocytes were incubated in 0.3 ml KRH/3% FAA-free BSA for 0-2 hours at 37° C. and shaken at 150 rpm. At the end of the incubation, glycerol and NEFA released into the infranatant were measured with the Free Glycerol Reagent (Sigma) and the Nonesterified Fatty Acids Kit (Catachem), respectively.

B. Results

1. Effects of Chemical Modification for siRNAs

Serum Stability Test

ITRI-1, ITRI-2 and ITRI-3 siRNAs (unmodified form and modified form) (1 μM) were incubated at 37° C. in 50% serum of different species (human, mouse or fetal bovine serums) to determine the stability of the unmodified form and modified form siRNAs in serum of different species. The derailed experimental method was described above. The results of the stability tests of the unmodified form and modified form siRNAs in human serum, mouse serum and fetal bovine serums are shown in FIGS. 1A, 1B and 1C, respectively.

Figure 1A:
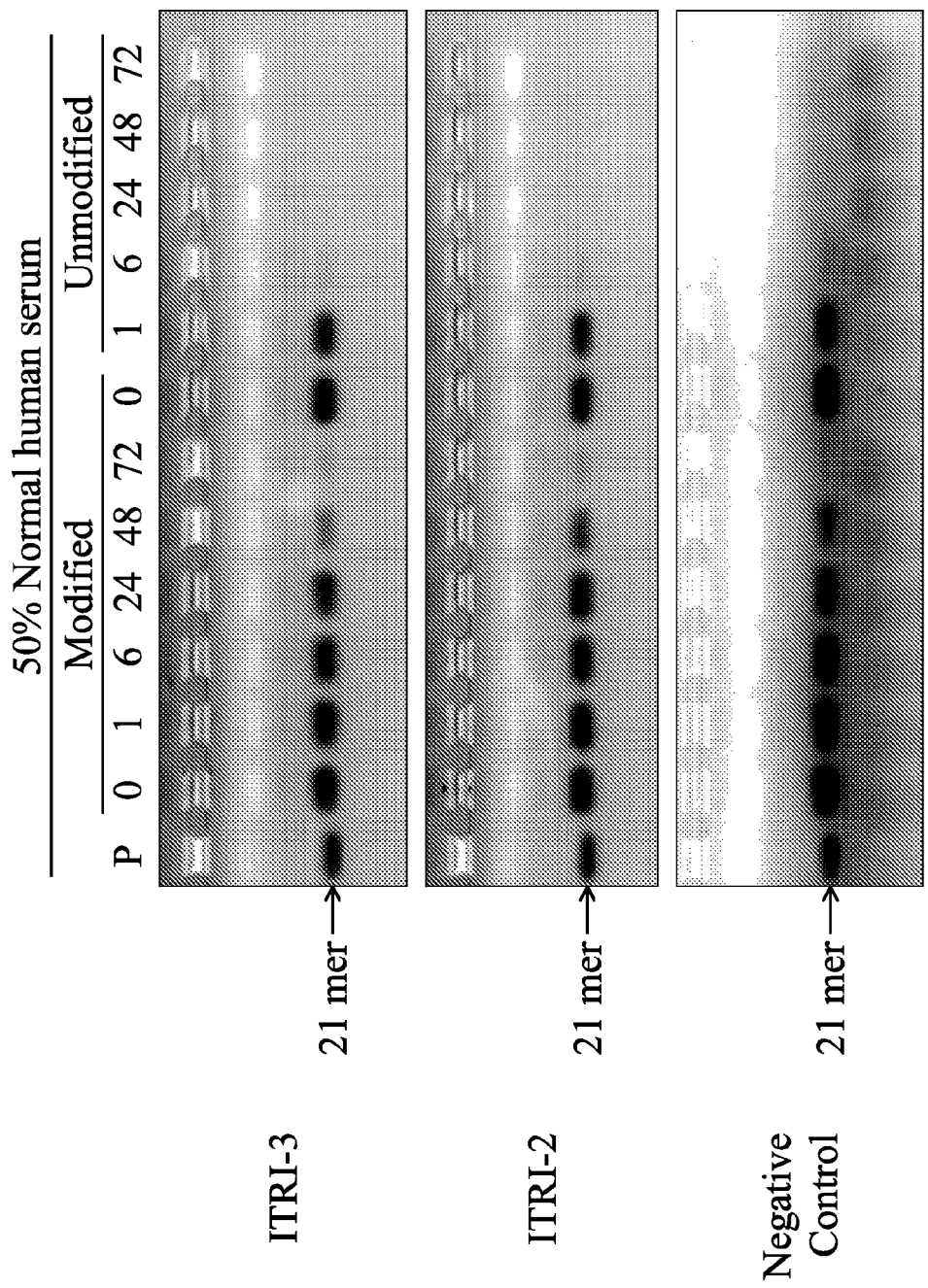
FIG. 1A shows the results of the stability tests of the unmodified form and modified form siRNAs in human serum according to one embodiment of the present disclosure.
Figure 1B:
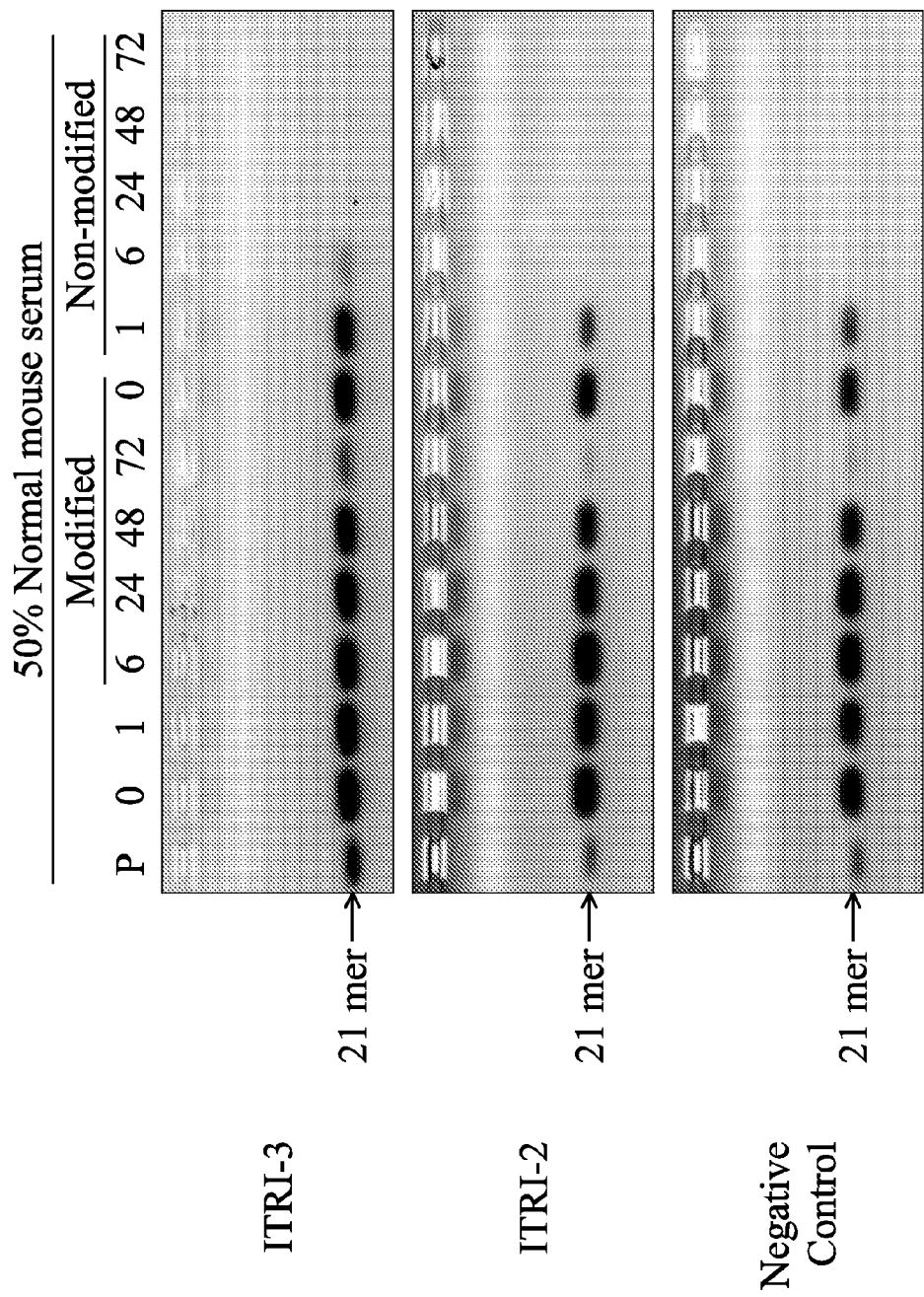
FIG. 1B shows the results of the stability tests of the unmodified form and modified form siRNAs in mouse serum according to one embodiment of the present disclosure.
Figure 1C:
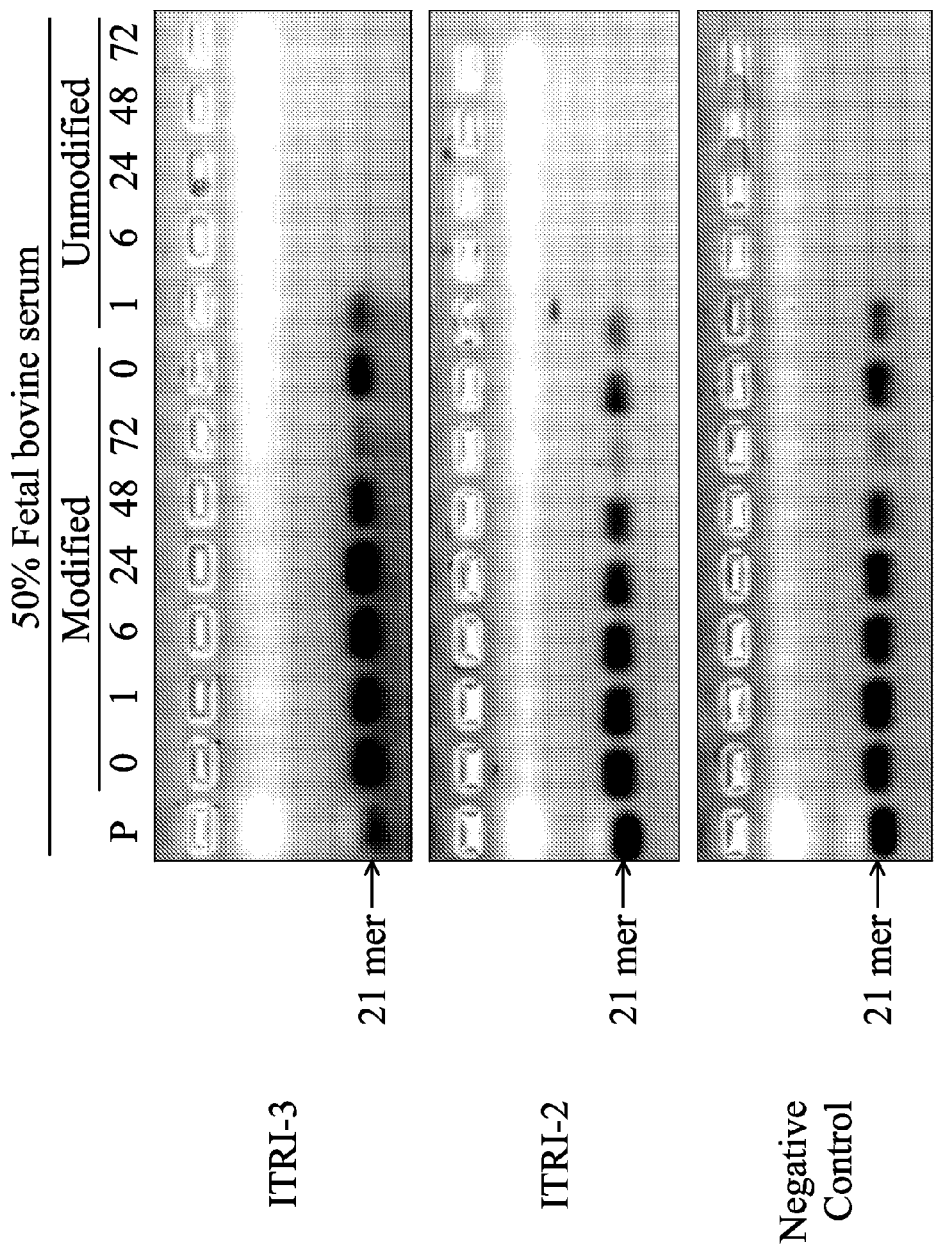
FIG. 1C shows the results of the stability tests of the unmodified form and modified form siRNAs in fetal bovine serum according to one embodiment of the present disclosure.

FIGS. 1A, 1B and 1C show that, compared with the unmodified form siRNAs (>6 hours), the modified form siRNAs (about 72 hours) show raised stability in serums.

2. Knock Down of Galectin-12 in Induced Differentiated Adipocytes 150 nM of negative control siRNA (unmodified form and modified form) and ITRI-3 galectin-12_siRNA (unmodified form and modified form) were delivered into NIH-3T3-L3 cell derived adipocytes, 130 and 170 nM of negative control siRNA (unmodified form and modified form) and ITRI-3 galectin-12_siRNA (unmodified form and modified form) were delivered into human mesenchymal stem cell derived adipocytes, and 150 nM of negative control siRNA (unmodified form) and siRNA-1, ITRI-1, ITRI-2, ITRI-3 galectin-12_siRNAs (unmodified form) were delivered into human mesenchymal stem cell derived adipocytes, and then mRNA expression levels of galectin-12 of NIH-3T3-L1 cell derived adipocytes and human mesenchymal stem cell derived adipocytes were determined, respectively. The derailed experimental method was described above.

mRNA expression levels of galectin-12 of NIH-3T3-L1 cell derived adipocytes transfected with negative control siRNA (unmodified form and modified form) and ITRI-3 galectin-12_siRNA (unmodified form and modified form) are shown in FIG. 2A.

In addition, mRNA expression levels of galectin-12 of human mesenchymal stem cell derived adipocytes transfected with negative control siRNA (unmodified form and modified form) and ITRI-3 galectin-12_siRNA (unmodified form and modified form) are shown in FIG. 2B.

Furthermore, mRNA expression levels of galectin-12 of human mesenchymal stem cell derived adipocytes transfected with negative control siRNA (unmodified form) and siRNA-1, ITRI-1, ITRI-2, ITRI-3 galectin-12_siRNAs (unmodified form) are shown in FIG. 2C According to FIG. 2A and FIG. 2B, it is known that modified form ITRI-3 galectin-12_siRNA in vitro significantly inhibited endogenous mRNA expression levels of galectin-12 of adipocytes of two different species, mouse and human.

Moreover, based on FIG. 2C, it is known that unmodified form siRNA-1, ITRI-1, ITRI-2, ITRI-3 galectin-12_siRNAs are all capable of in vitro inhibiting endogenous mRNA expression levels of galectin-12 of adipocytes of human, significantly.

3. Ex Vivo Knock Down Galectin-12 in Mouse Adipose Tissue

Tissue explants of epididymal fat pad obtained from 10-week-old male C57 BL/6J mice were transfected with 16 nmol negative control siRNA (modified form) or ITRI-3 siRNA (modified form) by electroporation at 50V and 80V, and then were incubated at 37° C. in 5% $CO_2$. After that the mRNA expression levels of galectin-12 of the tissue explants transfected with 16 nmol negative control siRNA (modified form) and ITRI-3 siRNA (modified form) were determined. The derailed experimental method is described above.

The mRNA expression levels of galectin-12 of the tissue explants (mouse adipose tissue) transfected with negative control siRNA (modified form) and ITRI-3 siRNA (modified form) by electroporation at 50V and 80V are shown in FIG. 3.

FIG. 3 shows that modified form ITRI-3 siRNA inhibit mRNA expression levels of galectin-12 of mouse adipose tissue, significantly at both two different electroporation condition (50V and 80V).

4. In Vivo Knockdown Galectin-12 in Mouse Adipose Tissue

Fifteen 10-week-old male mice were randomly assigned to 5 groups receiving PBS buffer, 26 mg/kg negative control siRNA (modified form), 26 mg/kg ITRI-3 galectin-12_siRNA (modified form), 13 mg/kg negative control siRNA (modified form) and 13 mg/kg ITRI-3 galectin-12_siRNA (modified form), and then the mRNA expression levels of galectin-12 of the tissues from the mice were determined. The derailed experimental method was described above.

The mRNA expression levels of galectin-12 of the adipose tissues of mice receiving PBS buffer, 26 mg/kg negative control siRNA (modified form), 26 mg/kg ITRI-3 galectin-12_siRNA (modified form), 13 mg/kg negative control siRNA (modified form) and 13 mg/kg ITRI-3 galectin-12_siRNA (modified form) are shown in FIG. 4.

FIG. 4 shows that, compared to the modified-form negative control siRNA, the two doses (26 mg/kg and 13 mg/kg) of modified-form ITRI-3 siRNA are both able to inhibit mRNA expression levels of galectin-12 of adipose tissue in vivo, and the inhibiting rate of the two doses (26 mg/kg and 13 mg/kg) to mRNA expression levels of galectin-12 can reach 60%. This result shows that modified-form ITRI-3 siRNA can correctly inhibit mRNA expression levels of galectin-12 of topical adipose tissues through the peripheral circulatory system by systemic administration.

5. In Vivo Knockdown Galectin-12 Induces Lipolysis of Mouse Adipose Tissue in Obesity Animal Mode Twenty 6-week-old male mice were fattened with high-fat diet feeding stuff for eight weeks to increase the body weight to about 40 g, and then randomly assigned to 4 groups receiving 1.08 mg/kg negative control siRNA (modified form), 1.08 mg/kg ITRI-3 galectin-12_siRNA (modified form), 9 mg/kg negative control siRNA (modified form) and 9 mg/kg ITRI-3 galectin-12_siRNA (modified form), and five 14-week-old male mice which were not fattened with high-fat diet feeding were assigned to a PBS receiving buffer group as a negative control group. After that, the mRNA expression levels of galectin-12 and lipolysis level of the tissues from the mice were determined. The detailed experimental method was described above.

The mRNA expression levels of galectin-12 of the adipose tissues of mice receiving 1.08 mg/kg negative control siRNA (modified form), 1.08 mg/kg ITRI-3 galectin-12_siRNA (modified form), 9 mg/kg negative control siRNA (modified form) and 9 mg/kg ITRI-3 galectin-12_siRNA (modified form) are shown in FIG. 5A.

FIG. 5A shows that, compared to modified-form negative control siRNA, the two doses (1.08 mg/kg and 9 mg/kg) of modified-form ITRI-3 siRNA are both able to inhibit mRNA expression levels of galectin-12 of adipose tissue in vivo, and the inhibiting rate of the two doses (1.08 mg/kg and 9 mg/kg) to mRNA expression levels of galectin-12 can reach 30%. This result shows that modified-form ITRI-3 siRNA can correctly inhibit mRNA expression levels of galectin-12 of topical adipose tissues through the peripheral circulatory system by systemic administration in obesity animal mode.

The lipolysis assay results of the adipose tissues of mice receiving PBS buffer, 1.08 mg/kg negative control siRNA (modified form), 1.08 mg/kg ITRI-3 galectin-12_siRNA (modified form), 9 mg/kg negative control siRNA (modified form) and 9 mg/kg ITRI-3 galectin-12_siRNA (modified form) are shown in FIG. 5B.

FIG. 5B shows that, compared to modified-form negative control siRNA, the two doses (1.08 mg/kg and 9 mg/kg) of modified-form ITRI-3 siRNA are both capable of enhancing lipolysis of adipose tissue in vivo.

This result shows that modified-form ITRI-3 siRNA can not only inhibit expression of galectin-12 mRNA of adipose tissues by systemic administration, but it can also change the lipid metabolism of adipocytes to enhance lipolysis, and that supports application for diet.

Furthermore, hematoxylin and eosin stains (H&E stains) were performed on adipose tissue biopsy of the mice receiving PBS buffer, 1.08 mg/kg negative control siRNA (modified form), 1.08 mg/kg ITRI-3 galectin-12_siRNA (modified form), 9 mg/kg negative control siRNA (modified form) and 9 mg/kg ITRI-3 galectin-12_siRNA (modified form) mentioned above, and the results are shown in FIG. 5C.

FIG. 5C shows that, compared to the adipose tissues of mice receiving negative control siRNA (modified form), the adipose tissues of mice receiving ITRI-3 galectin-12_siRNA (modified form) shows more shrinkage, and the adipose tissues of mice of the group receiving 9 mg/kg ITRI-3 galectin-12_siRNA (modified form) underwent the most shrinkage. This result shows that modified-form ITRI-3 siRNA can not only inhibit expression of galectin-12 mRNA of adipose tissues by systemic administration, but it can also change the lipid metabolism of adipocytes to enhance lipolysis by inhibiting expression of galectin-12 mRNA of the adipose tissues, and that supports application for diet.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A small interfering RNA (siRNA), consisting of a passenger strand and a guide strand,
wherein the sequence of the passenger strand comprises the sequence of SEQ ID NO. 7, and the sequence of the guide strand comprises the sequence of SEQ ID NO. 8, wherein the small interfering RNA is capable of inhibiting galectin-12 expression.

2. The small interfering RNA as claimed in claim 1, wherein the sequence of the passenger strand is SEQ ID NO. 7 and the sequence of the guide strand is SEQ ID NO. 8, or wherein the sequence of the passenger strand is SEQ ID NO. 23 and the sequence of the guide strand is SEQ ID NO. 24.

3. The small interfering RNA as claimed in claim 1, wherein the passenger strand and/or the guide strand comprises at least one modified nucleotide and/or at least one modified phosphodiester bond.

4. The small interfering RNA as claimed in claim 3, wherein the at least one modified nucleotide is a 2'-O-methyl nucleotide, 5'-O-methylphosphonate nucleic acid, peptide nucleic acid (PNA), N-Morpholino or locked nucleic acid (LNA).

5. The small interfering RNA as claimed in claim 3, wherein the at least one modified phosphodiester bond is a phosphorothioate bond, boranophosphate bond, PNA bond or morpholino bond.

6. The small interfering RNA as claimed in claim 3, wherein the at least one modified nucleotide is a 2'-O-methyl nucleotide and/or the at least one modified phosphodiester bond is a phosphorothioate bond.

7. The small interfering RNA as claimed in claim 6, wherein the sequence of the passenger strand is SEQ ID NO. 15 and the sequence of the guide strand is SEQ ID NO. 16, or wherein the sequence of the passenger strand is SEQ ID NO. 31 and the sequence of the guide strand is SEQ ID NO. 32.

8. The small interfering RNA as claimed in claim 1, wherein the small interfering RNA is formulated into a medicament alone or with a pharmaceutically acceptable carrier or salt.

9. A pharmaceutical composition for inhibiting galectin-12 expression and/or enhancing lipolysis, comprising:
the small interfering RNA as claimed in claim 1.

10. The pharmaceutical composition for inhibiting galectin-12 expression and/or enhancing lipolysis as claimed in claim 9, wherein the sequence of the passenger strand is SEQ ID NO. 7 and the sequence of the guide strand is SEQ ID NO. 8, or wherein the sequence of the passenger strand is SEQ ID NO. 23 and the sequence of the guide strand is SEQ ID NO. 24.

11. The pharmaceutical composition for inhibiting galectin-12 expression and/or enhancing lipolysis as claimed in claim 9, wherein the passenger strand and/or the guide strand comprises at least one modified nucleotide and/or at least one modified phosphodiester bond, wherein the at least one modified nucleotide is a 2'-O-methyl nucleotide and/or the at least one modified phosphodiester bond is a phosphorothioate bond.

12. The pharmaceutical composition for inhibiting galectin-12 expression and/or enhancing lipolysis as claimed in claim 11, wherein the sequence of the passenger strand is SEQ ID NO. 15 and the sequence of the guide strand is SEQ ID NO. 16, or wherein the sequence of the passenger strand is SEQ ID NO. 31 and the sequence of the guide strand is SEQ ID NO. 32.

13. The pharmaceutical composition for inhibiting galectin-12 expression and/or enhancing lipolysis as claimed in claim 9, further comprising a pharmaceutically acceptable carrier or salt.

14. The pharmaceutical composition for inhibiting galectin-12 expression and/or enhancing lipolysis as claimed in claim 13, wherein the pharmaceutically acceptable carrier comprising a liposome, micelle, metal particle or polymer particle.

15. A method for inhibiting galectin-12 expression and/or enhancing lipolysis, comprising:
administering an effective amount of the pharmaceutical composition as claimed in claim 9 to a subject in need.

16. The method for inhibiting galectin-12 expression and/or enhancing lipolysis as claimed in claim 15, wherein the subject in need suffers from obesity.

17. The method for inhibiting galectin-12 expression and/or enhancing lipolysis as claimed in claim 15, wherein the sequence of the passenger strand is SEQ ID NO. 7 and the sequence of the guide strand is SEQ ID NO. 8, or wherein the sequence of the passenger strand is SEQ ID NO. 23 and the sequence of the guide strand is SEQ ID NO. 24.

18. The method for inhibiting galectin-12 expression and/or enhancing lipolysis as claimed in claim 15, wherein the passenger strand and/or the guide strand comprises at least one modified nucleotide and/or at least one modified phosphodiester bond, wherein the at least one modified nucleotide is a 2'-O-methyl nucleotide and/or the at least one modified phosphodiester bond is a phosphorothioate bond.

19. The method for inhibiting galectin-12 expression and/or enhancing lipolysis as claimed in claim 18, wherein the sequence of the passenger strand is SEQ ID NO. 15 and the sequence of the guide strand is SEQ ID NO. 16, or wherein the sequence of the passenger strand is SEQ ID NO. 31 and the sequence of the guide strand is SEQ ID NO. 32.

20. The method for inhibiting galectin-12 expression and/or enhancing lipolysis as claimed in claim 15, wherein the pharmaceutical composition further comprises a pharmaceutically acceptable carrier or salt.

21. The method for inhibiting galectin-12 expression and/or enhancing lipolysis as claimed in claim 20, wherein the pharmaceutically acceptable carrier comprising a liposome, micelle, metal particle or polymer particle.

* * * * *

SEQUENCE LISTING

```
<160> NUMBER OF SEQ ID NOS: 36

<210> SEQ ID NO 1
<211> LENGTH: 19
<212> TYPE: RNA
<213> ORGANISM: Artificial Sequence
<220> FEATURE:
```

```
<223> OTHER INFORMATION: siRNA passenger strand

<400> SEQUENCE: 1
ugggcagguc aucauagua                                                  19

<210> SEQ ID NO 2
<211> LENGTH: 19
<212> TYPE: RNA
<213> ORGANISM: Artificial Sequence
<220> FEATURE:
<223> OTHER INFORMATION: siRNA guide strand

<400> SEQUENCE: 2
uacuaugaug accugccca                                                  19

<210> SEQ ID NO 3
<211> LENGTH: 19
<212> TYPE: RNA
<213> ORGANISM: Artificial Sequence
<220> FEATURE:
<223> OTHER INFORMATION: siRNA passenger strand

<400> SEQUENCE: 3
gugguuccuu augucacga                                                  19

<210> SEQ ID NO 4
<211> LENGTH: 19
<212> TYPE: RNA
<213> ORGANISM: Artificial Sequence
<220> FEATURE:
<223> OTHER INFORMATION: siRNA guide strand

<400> SEQUENCE: 4
ucgugacaua aggaaccac                                                  19

<210> SEQ ID NO 5
<211> LENGTH: 19
<212> TYPE: RNA
<213> ORGANISM: Artificial Sequence
<220> FEATURE:
<223> OTHER INFORMATION: siRNA passenger strand

<400> SEQUENCE: 5
gggcagaaga aacugaucu                                                  19

<210> SEQ ID NO 6
<211> LENGTH: 19
<212> TYPE: RNA
<213> ORGANISM: Artificial Sequence
<220> FEATURE:
<223> OTHER INFORMATION: siRNA guide strand

<400> SEQUENCE: 6
agaucaguuu cuucugccc                                                  19

<210> SEQ ID NO 7
<211> LENGTH: 19
<212> TYPE: RNA
<213> ORGANISM: Artificial Sequence
<220> FEATURE:
<223> OTHER INFORMATION: siRNA passenger strand

<400> SEQUENCE: 7
cuguuggauu ccugaacau                                                  19
```

-continued

```
<210> SEQ ID NO 8
<211> LENGTH: 19
<212> TYPE: RNA
<213> ORGANISM: Artificial Sequence
<220> FEATURE:
<223> OTHER INFORMATION: siRNA guide strand

<400> SEQUENCE: 8
auguucagga auccaacag                                                    19

<210> SEQ ID NO 9
<211> LENGTH: 19
<212> TYPE: RNA
<213> ORGANISM: Artificial Sequence
<220> FEATURE:
<223> OTHER INFORMATION: siRNA passenger strand
<220> FEATURE:
<221> NAME/KEY: modified_base
<222> LOCATION: (1)..(1)
<223> OTHER INFORMATION: um
<220> FEATURE:
<221> NAME/KEY: misc_difference
<222> LOCATION: (1)..(2)
<223> OTHER INFORMATION: phosphorothioate bond
<220> FEATURE:
<221> NAME/KEY: modified_base
<222> LOCATION: (2)..(3)
<223> OTHER INFORMATION: gm
<220> FEATURE:
<221> NAME/KEY: misc_difference
<222> LOCATION: (2)..(3)
<223> OTHER INFORMATION: phosphorothioate bond
<220> FEATURE:
<221> NAME/KEY: misc_difference
<222> LOCATION: (3)..(4)
<223> OTHER INFORMATION: phosphorothioate bond
<220> FEATURE:
<221> NAME/KEY: misc_difference
<222> LOCATION: (5)..(6)
<223> OTHER INFORMATION: phosphorothioate bond
<220> FEATURE:
<221> NAME/KEY: modified_base
<222> LOCATION: (9)..(9)
<223> OTHER INFORMATION: um
<220> FEATURE:
<221> NAME/KEY: modified_base
<222> LOCATION: (12)..(12)
<223> OTHER INFORMATION: um
<220> FEATURE:
<221> NAME/KEY: misc_difference
<222> LOCATION: (17)..(18)
<223> OTHER INFORMATION: phosphorothioate bond

<400> SEQUENCE: 9
ugggcagguc aucauagua                                                    19

<210> SEQ ID NO 10
<211> LENGTH: 19
<212> TYPE: RNA
<213> ORGANISM: Artificial Sequence
<220> FEATURE:
<223> OTHER INFORMATION: siRNA guide strand
<220> FEATURE:
<221> NAME/KEY: modified_base
<222> LOCATION: (2)..(2)
<223> OTHER INFORMATION: 2'-O-methyl-adenosine
<220> FEATURE:
<221> NAME/KEY: modified_base
<222> LOCATION: (18)..(18)
<223> OTHER INFORMATION: cm
<220> FEATURE:
<221> NAME/KEY: modified_base
<222> LOCATION: (19)..(19)
<223> OTHER INFORMATION: 2'-O-methyl-adenosine
```

```
<400> SEQUENCE: 10
uacuaugaug accugccca                                              19

<210> SEQ ID NO 11
<211> LENGTH: 19
<212> TYPE: RNA
<213> ORGANISM: Artificial Sequence
<220> FEATURE:
<223> OTHER INFORMATION: siRNA passenger strand
<220> FEATURE:
<221> NAME/KEY: modified_base
<222> LOCATION: (1)..(1)
<223> OTHER INFORMATION: gm
<220> FEATURE:
<221> NAME/KEY: misc_difference
<222> LOCATION: (1)..(2)
<223> OTHER INFORMATION: phosphorothioate bond
<220> FEATURE:
<221> NAME/KEY: modified_base
<222> LOCATION: (2)..(2)
<223> OTHER INFORMATION: um
<220> FEATURE:
<221> NAME/KEY: misc_difference
<222> LOCATION: (2)..(3)
<223> OTHER INFORMATION: phosphorothioate bond
<220> FEATURE:
<221> NAME/KEY: modified_base
<222> LOCATION: (3)..(3)
<223> OTHER INFORMATION: gm
<220> FEATURE:
<221> NAME/KEY: misc_difference
<222> LOCATION: (3)..(4)
<223> OTHER INFORMATION: phosphorothioate bond
<220> FEATURE:
<221> NAME/KEY: misc_difference
<222> LOCATION: (5)..(6)
<223> OTHER INFORMATION: phosphorothioate bond
<220> FEATURE:
<221> NAME/KEY: modified_base
<222> LOCATION: (9)..(9)
<223> OTHER INFORMATION: um
<220> FEATURE:
<221> NAME/KEY: modified_base
<222> LOCATION: (12)..(12)
<223> OTHER INFORMATION: um
<220> FEATURE:
<221> NAME/KEY: misc_difference
<222> LOCATION: (17)..(18)
<223> OTHER INFORMATION: phosphorothioate bond

<400> SEQUENCE: 11
gugguuccuu augucacga                                              19

<210> SEQ ID NO 12
<211> LENGTH: 19
<212> TYPE: RNA
<213> ORGANISM: Artificial Sequence
<220> FEATURE:
<223> OTHER INFORMATION: siRNA guide strand
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (18)..(18)
<223> OTHER INFORMATION: 2'-O-methyl-adenosine
<220> FEATURE:
<221> NAME/KEY: modified_base
<222> LOCATION: (19)..(19)
<223> OTHER INFORMATION: cm

<400> SEQUENCE: 12
ucgugacaua aggaaccac                                              19
```

<210> SEQ ID NO 13
<211> LENGTH: 19
<212> TYPE: RNA
<213> ORGANISM: Artificial Sequence
<220> FEATURE:
<223> OTHER INFORMATION: siRNA passenger strand
<220> FEATURE:
<221> NAME/KEY: modified_base
<222> LOCATION: (1)..(1)
<223> OTHER INFORMATION: gm
<220> FEATURE:
<221> NAME/KEY: misc_difference
<222> LOCATION: (1)..(2)
<223> OTHER INFORMATION: phosphorothioate bond
<220> FEATURE:
<221> NAME/KEY: modified_base
<222> LOCATION: (2)..(2)
<223> OTHER INFORMATION: gm
<220> FEATURE:
<221> NAME/KEY: misc_difference
<222> LOCATION: (2)..(3)
<223> OTHER INFORMATION: phosphorothioate bond
<220> FEATURE:
<221> NAME/KEY: modified_base
<222> LOCATION: (3)..(3)
<223> OTHER INFORMATION: gm
<220> FEATURE:
<221> NAME/KEY: misc_difference
<222> LOCATION: (3)..(4)
<223> OTHER INFORMATION: phosphorothioate bond
<220> FEATURE:
<221> NAME/KEY: misc_difference
<222> LOCATION: (5)..(6)
<223> OTHER INFORMATION: phosphorothioate bond
<220> FEATURE:
<221> NAME/KEY: modified_base
<222> LOCATION: (9)..(9)
<223> OTHER INFORMATION: gm
<220> FEATURE:
<221> NAME/KEY: modified_base
<222> LOCATION: (12)..(12)
<223> OTHER INFORMATION: 2'-O-methyl-adenosine
<220> FEATURE:
<221> NAME/KEY: misc_difference
<222> LOCATION: (17)..(18)
<223> OTHER INFORMATION: phosphorothioate bond

<400> SEQUENCE: 13
gggcagaaga aacugaucu                                               19

<210> SEQ ID NO 14
<211> LENGTH: 19
<212> TYPE: RNA
<213> ORGANISM: Artificial Sequence
<220> FEATURE:
<223> OTHER INFORMATION: siRNA guide strand
<220> FEATURE:
<221> NAME/KEY: modified_base
<222> LOCATION: (2)..(2)
<223> OTHER INFORMATION: gm
<220> FEATURE:
<221> NAME/KEY: modified_base
<222> LOCATION: (18)..(18)
<223> OTHER INFORMATION: cm
<220> FEATURE:
<221> NAME/KEY: modified_base
<222> LOCATION: (19)..(19)
<223> OTHER INFORMATION: cm

<400> SEQUENCE: 14
agaucaguuu cuucugccc                                               19

<210> SEQ ID NO 15

```
<211> LENGTH: 19
<212> TYPE: RNA
<213> ORGANISM: Artificial Sequence
<220> FEATURE:
<223> OTHER INFORMATION: siRNA passenger strand
<220> FEATURE:
<221> NAME/KEY: modified_base
<222> LOCATION: (1)..(1)
<223> OTHER INFORMATION: cm
<220> FEATURE:
<221> NAME/KEY: misc_difference
<222> LOCATION: (1)..(2)
<223> OTHER INFORMATION: phosphorothioate bond
<220> FEATURE:
<221> NAME/KEY: modified_base
<222> LOCATION: (2)..(2)
<223> OTHER INFORMATION: um
<220> FEATURE:
<221> NAME/KEY: misc_difference
<222> LOCATION: (2)..(3)
<223> OTHER INFORMATION: phosphorothioate bond
<220> FEATURE:
<221> NAME/KEY: modified_base
<222> LOCATION: (3)..(3)
<223> OTHER INFORMATION: gm
<220> FEATURE:
<221> NAME/KEY: misc_difference
<222> LOCATION: (3)..(4)
<223> OTHER INFORMATION: phosphorothioate bond
<220> FEATURE:
<221> NAME/KEY: misc_difference
<222> LOCATION: (5)..(6)
<223> OTHER INFORMATION: phosphorothioate bond
<220> FEATURE:
<221> NAME/KEY: modified_base
<222> LOCATION: (9)..(9)
<223> OTHER INFORMATION: um
<220> FEATURE:
<221> NAME/KEY: modified_base
<222> LOCATION: (12)..(12)
<223> OTHER INFORMATION: cm
<220> FEATURE:
<221> NAME/KEY: misc_difference
<222> LOCATION: (17)..(18)
<223> OTHER INFORMATION: phosphorothioate bond

<400> SEQUENCE: 15 cguuggauu ccugaacau                                                 19

<210> SEQ ID NO 16
<211> LENGTH: 19
<212> TYPE: RNA
<213> ORGANISM: Artificial Sequence
<220> FEATURE:
<223> OTHER INFORMATION: siRNA guide strand
<220> FEATURE:
<221> NAME/KEY: modified_base
<222> LOCATION: (2)..(2)
<223> OTHER INFORMATION: um
<220> FEATURE:
<221> NAME/KEY: modified_base
<222> LOCATION: (18)..(18)
<223> OTHER INFORMATION: 2'-O-methyl-adenosine
<220> FEATURE:
<221> NAME/KEY: modified_base
<222> LOCATION: (19)..(19)
<223> OTHER INFORMATION: gm

<400> SEQUENCE: 16
auguucagga auccaacag                                                19

<210> SEQ ID NO 17
<211> LENGTH: 21
<212> TYPE: RNA
<213> ORGANISM: Artificial Sequence
```

```
<220> FEATURE:
<223> OTHER INFORMATION: siRNA passenger strand
<220> FEATURE:
<221> NAME/KEY: modified_base
<222> LOCATION: (20)..(21)
<223> OTHER INFORMATION: thymine deoxyribonucleotide (dT)

<400> SEQUENCE: 17
ugggcagguc aucauaguan n                                              21

<210> SEQ ID NO 18
<211> LENGTH: 21
<212> TYPE: RNA
<213> ORGANISM: Artificial Sequence
<220> FEATURE:
<223> OTHER INFORMATION: siRNA guide strand
<220> FEATURE:
<221> NAME/KEY: modified_base
<222> LOCATION: (20)..(21)
<223> OTHER INFORMATION: thymine deoxyribonucleotide (dT)

<400> SEQUENCE: 18
uacuaugaug accugcccan n                                              21

<210> SEQ ID NO 19
<211> LENGTH: 21
<212> TYPE: RNA
<213> ORGANISM: Artificial Sequence
<220> FEATURE:
<223> OTHER INFORMATION: siRNA passenger strand
<220> FEATURE:
<221> NAME/KEY: modified_base
<222> LOCATION: (20)..(21)
<223> OTHER INFORMATION: thymine deoxyribonucleotide (dT)

<400> SEQUENCE: 19
gugguuccuu augucacgan n                                              21

<210> SEQ ID NO 20
<211> LENGTH: 21
<212> TYPE: RNA
<213> ORGANISM: Artificial Sequence
<220> FEATURE:
<223> OTHER INFORMATION: siRNA guide strand
<220> FEATURE:
<221> NAME/KEY: modified_base
<222> LOCATION: (20)..(21)
<223> OTHER INFORMATION: thymine deoxyribonucleotide (dT)

<400> SEQUENCE: 20
ucgugacaua aggaaccacn n                                              21

<210> SEQ ID NO 21
<211> LENGTH: 21
<212> TYPE: RNA
<213> ORGANISM: Artificial Sequence
<220> FEATURE:
<223> OTHER INFORMATION: siRNA passenger strand
<220> FEATURE:
<221> NAME/KEY: modified_base
<222> LOCATION: (20)..(21)
<223> OTHER INFORMATION: thymine deoxyribonucleotide (dT)

<400> SEQUENCE: 21
gggcagaaga aacugaucun n                                              21

<210> SEQ ID NO 22
<211> LENGTH: 21
<212> TYPE: RNA
```

```
<213> ORGANISM: Artificial Sequence
<220> FEATURE:
<223> OTHER INFORMATION: siRNA guide strand
<220> FEATURE:
<221> NAME/KEY: modified_base
<222> LOCATION: (20)..(21)
<223> OTHER INFORMATION: thymine deoxyribonucleotide (dT)

<400> SEQUENCE: 22
agaucaguuu cuucugcccn n                                                  21

<210> SEQ ID NO 23
<211> LENGTH: 21
<212> TYPE: RNA
<213> ORGANISM: Artificial Sequence
<220> FEATURE:
<223> OTHER INFORMATION: siRNA passenger strand
<220> FEATURE:
<221> NAME/KEY: modified_base
<222> LOCATION: (20)..(21)
<223> OTHER INFORMATION: thymine deoxyribonucleotide (dT)

<400> SEQUENCE: 23 cguuggauu ccugaacaun n                                                   21

<210> SEQ ID NO 24
<211> LENGTH: 21
<212> TYPE: RNA
<213> ORGANISM: Artificial Sequence
<220> FEATURE:
<223> OTHER INFORMATION: siRNA guide strand
<220> FEATURE:
<221> NAME/KEY: modified_base
<222> LOCATION: (20)..(21)
<223> OTHER INFORMATION: thymine deoxyribonucleotide (dT)

<400> SEQUENCE: 24
auguucagga auccaacagn n                                                  21

<210> SEQ ID NO 25
<211> LENGTH: 21
<212> TYPE: RNA
<213> ORGANISM: Artificial Sequence
<220> FEATURE:
<223> OTHER INFORMATION: siRNA passenger strand
<220> FEATURE:
<221> NAME/KEY: modified_base
<222> LOCATION: (1)..(1)
<223> OTHER INFORMATION: um
<220> FEATURE:
<221> NAME/KEY: misc_difference
<222> LOCATION: (1)..(2)
<223> OTHER INFORMATION: phosphorothioate bond
<220> FEATURE:
<221> NAME/KEY: modified_base
<222> LOCATION: (2)..(3)
<223> OTHER INFORMATION: gm
<220> FEATURE:
<221> NAME/KEY: misc_difference
<222> LOCATION: (2)..(3)
<223> OTHER INFORMATION: phosphorothioate bond
<220> FEATURE:
<221> NAME/KEY: misc_difference
<222> LOCATION: (3)..(4)
<223> OTHER INFORMATION: phosphorothioate bond
<220> FEATURE:
<221> NAME/KEY: misc_difference
<222> LOCATION: (5)..(6)
<223> OTHER INFORMATION: phosphorothioate bond
<220> FEATURE:
<221> NAME/KEY: modified_base
<222> LOCATION: (9)..(9)
<223> OTHER INFORMATION: um
```

```
<220> FEATURE:
<221> NAME/KEY: modified_base
<222> LOCATION: (12)..(12)
<223> OTHER INFORMATION: um
<220> FEATURE:
<221> NAME/KEY: misc_difference
<222> LOCATION: (17)..(18)
<223> OTHER INFORMATION: phosphorothioate bond
<220> FEATURE:
<221> NAME/KEY: misc_difference
<222> LOCATION: (19)..(20)
<223> OTHER INFORMATION: phosphorothioate bond
<220> FEATURE:
<221> NAME/KEY: misc_difference
<222> LOCATION: (20)..(21)
<223> OTHER INFORMATION: phosphorothioate bond
<220> FEATURE:
<221> NAME/KEY: modified_base
<222> LOCATION: (20)..(21)
<223> OTHER INFORMATION: thymine deoxyribonucleotide (dT)

<400> SEQUENCE: 25
ugggcagguc aucauaguan n                                              21

<210> SEQ ID NO 26
<211> LENGTH: 21
<212> TYPE: RNA
<213> ORGANISM: Artificial Sequence
<220> FEATURE:
<223> OTHER INFORMATION: siRNA guide strand
<220> FEATURE:
<221> NAME/KEY: modified_base
<222> LOCATION: (2)..(2)
<223> OTHER INFORMATION: 2'-O-methyl-adenosine
<220> FEATURE:
<221> NAME/KEY: modified_base
<222> LOCATION: (18)..(18)
<223> OTHER INFORMATION: cm
<220> FEATURE:
<221> NAME/KEY: modified_base
<222> LOCATION: (19)..(19)
<223> OTHER INFORMATION: 2'-O-methyl-adenosine
<220> FEATURE:
<221> NAME/KEY: misc_difference
<222> LOCATION: (19)..(20)
<223> OTHER INFORMATION: phosphorothioate bond
<220> FEATURE:
<221> NAME/KEY: modified_base
<222> LOCATION: (20)..(21)
<223> OTHER INFORMATION: thymine deoxyribonucleotide (dT)
<220> FEATURE:
<221> NAME/KEY: misc_difference
<222> LOCATION: (20)..(21)
<223> OTHER INFORMATION: phosphorothioate bond

<400> SEQUENCE: 26
uacuaugaug accugcccan n                                              21

<210> SEQ ID NO 27
<211> LENGTH: 21
<212> TYPE: RNA
<213> ORGANISM: Artificial Sequence
<220> FEATURE:
<223> OTHER INFORMATION: siRNA passenger strand
<220> FEATURE:
<221> NAME/KEY: modified_base
<222> LOCATION: (1)..(1)
<223> OTHER INFORMATION: gm
<220> FEATURE:
<221> NAME/KEY: misc_difference
<222> LOCATION: (1)..(2)
<223> OTHER INFORMATION: phosphorothioate bond
<220> FEATURE:
<221> NAME/KEY: modified_base
<222> LOCATION: (2)..(2)
```

<223> OTHER INFORMATION: um
<220> FEATURE:
<221> NAME/KEY: misc_difference
<222> LOCATION: (2)..(3)
<223> OTHER INFORMATION: phosphorothioate bond
<220> FEATURE:
<221> NAME/KEY: modified_base
<222> LOCATION: (3)..(3)
<223> OTHER INFORMATION: gm
<220> FEATURE:
<221> NAME/KEY: misc_difference
<222> LOCATION: (3)..(4)
<223> OTHER INFORMATION: phosphorothioate bond
<220> FEATURE:
<221> NAME/KEY: misc_difference
<222> LOCATION: (5)..(6)
<223> OTHER INFORMATION: phosphorothioate bond
<220> FEATURE:
<221> NAME/KEY: modified_base
<222> LOCATION: (9)..(9)
<223> OTHER INFORMATION: um
<220> FEATURE:
<221> NAME/KEY: modified_base
<222> LOCATION: (12)..(12)
<223> OTHER INFORMATION: um
<220> FEATURE:
<221> NAME/KEY: misc_difference
<222> LOCATION: (17)..(18)
<223> OTHER INFORMATION: phosphorothioate bond
<220> FEATURE:
<221> NAME/KEY: misc_difference
<222> LOCATION: (19)..(20)
<223> OTHER INFORMATION: phosphorothioate bond
<220> FEATURE:
<221> NAME/KEY: modified_base
<222> LOCATION: (20)..(21)
<223> OTHER INFORMATION: thymine deoxyribonucleotide (dT)
<220> FEATURE:
<221> NAME/KEY: misc_difference
<222> LOCATION: (20)..(21)
<223> OTHER INFORMATION: phosphorothioate bond

<400> SEQUENCE: 27
gugguuccuu augucacgan n                                              21

<210> SEQ ID NO 28
<211> LENGTH: 21
<212> TYPE: RNA
<213> ORGANISM: Artificial Sequence
<220> FEATURE:
<223> OTHER INFORMATION: siRNA guide strand
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (18)..(18)
<223> OTHER INFORMATION: 2'-O-methyl-adenosine
<220> FEATURE:
<221> NAME/KEY: modified_base
<222> LOCATION: (19)..(19)
<223> OTHER INFORMATION: cm
<220> FEATURE:
<221> NAME/KEY: misc_difference
<222> LOCATION: (19)..(20)
<223> OTHER INFORMATION: phosphorothioate bond
<220> FEATURE:
<221> NAME/KEY: modified_base
<222> LOCATION: (20)..(21)
<223> OTHER INFORMATION: thymine deoxyribonucleotide (dT)
<220> FEATURE:
<221> NAME/KEY: misc_difference
<222> LOCATION: (20)..(21)
<223> OTHER INFORMATION: phosphorothioate bond

<400> SEQUENCE: 28
ucgugacaua aggaaccacn n                                                    21

<210> SEQ ID NO 29
<211> LENGTH: 21
<212> TYPE: RNA
<213> ORGANISM: Artificial Sequence
<220> FEATURE:
<223> OTHER INFORMATION: siRNA passenger strand
<220> FEATURE:
<221> NAME/KEY: modified_base
<222> LOCATION: (1)..(1)
<223> OTHER INFORMATION: gm
<220> FEATURE:
<221> NAME/KEY: misc_difference
<222> LOCATION: (1)..(2)
<223> OTHER INFORMATION: phosphorothioate bond
<220> FEATURE:
<221> NAME/KEY: modified_base
<222> LOCATION: (2)..(2)
<223> OTHER INFORMATION: gm
<220> FEATURE:
<221> NAME/KEY: misc_difference
<222> LOCATION: (2)..(3)
<223> OTHER INFORMATION: phosphorothioate bond
<220> FEATURE:
<221> NAME/KEY: modified_base
<222> LOCATION: (3)..(3)
<223> OTHER INFORMATION: gm
<220> FEATURE:
<221> NAME/KEY: misc_difference
<222> LOCATION: (3)..(4)
<223> OTHER INFORMATION: phosphorothioate bond
<220> FEATURE:
<221> NAME/KEY: misc_difference
<222> LOCATION: (5)..(6)
<223> OTHER INFORMATION: phosphorothioate bond
<220> FEATURE:
<221> NAME/KEY: modified_base
<222> LOCATION: (9)..(9)
<223> OTHER INFORMATION: gm
<220> FEATURE:
<221> NAME/KEY: modified_base
<222> LOCATION: (12)..(12)
<223> OTHER INFORMATION: 2'-O-methyl-adenosine
<220> FEATURE:
<221> NAME/KEY: misc_difference
<222> LOCATION: (17)..(18)
<223> OTHER INFORMATION: phosphorothioate bond
<220> FEATURE:
<221> NAME/KEY: misc_difference
<222> LOCATION: (19)..(20)
<223> OTHER INFORMATION: phosphorothioate bond
<220> FEATURE:
<221> NAME/KEY: modified_base
<222> LOCATION: (20)..(21)
<223> OTHER INFORMATION: thymine deoxyribonucleotide (dT)
<220> FEATURE:
<221> NAME/KEY: misc_difference
<222> LOCATION: (20)..(21)
<223> OTHER INFORMATION: phosphorothioate bond

<400> SEQUENCE: 29
gggcagaaga aacugaucun n                                                    21

<210> SEQ ID NO 30
<211> LENGTH: 21
<212> TYPE: RNA
<213> ORGANISM: Artificial Sequence
<220> FEATURE:
<223> OTHER INFORMATION: siRNA guide strand
<220> FEATURE:
<221> NAME/KEY: modified_base
<222> LOCATION: (2)..(2)
<223> OTHER INFORMATION: gm
<220> FEATURE:

```
<221> NAME/KEY: modified_base
<222> LOCATION: (18)..(18)
<223> OTHER INFORMATION: cm
<220> FEATURE:
<221> NAME/KEY: modified_base
<222> LOCATION: (19)..(19)
<223> OTHER INFORMATION: cm
<220> FEATURE:
<221> NAME/KEY: misc_difference
<222> LOCATION: (19)..(20)
<223> OTHER INFORMATION: phosphorothioate bond
<220> FEATURE:
<221> NAME/KEY: modified_base
<222> LOCATION: (20)..(21)
<223> OTHER INFORMATION: thymine deoxyribonucleotide (dT)
<220> FEATURE:
<221> NAME/KEY: misc_difference
<222> LOCATION: (20)..(21)
<223> OTHER INFORMATION: phosphorothioate bond

<400> SEQUENCE: 30
agaucaguuu cuucugcccn n                                              21

<210> SEQ ID NO 31
<211> LENGTH: 21
<212> TYPE: RNA
<213> ORGANISM: Artificial Sequence
<220> FEATURE:
<223> OTHER INFORMATION: siRNA passenger strand
<220> FEATURE:
<221> NAME/KEY: modified_base
<222> LOCATION: (1)..(1)
<223> OTHER INFORMATION: cm
<220> FEATURE:
<221> NAME/KEY: misc_difference
<222> LOCATION: (1)..(2)
<223> OTHER INFORMATION: phosphorothioate bond
<220> FEATURE:
<221> NAME/KEY: modified_base
<222> LOCATION: (2)..(2)
<223> OTHER INFORMATION: um
<220> FEATURE:
<221> NAME/KEY: misc_difference
<222> LOCATION: (2)..(3)
<223> OTHER INFORMATION: phosphorothioate bond
<220> FEATURE:
<221> NAME/KEY: modified_base
<222> LOCATION: (3)..(3)
<223> OTHER INFORMATION: gm
<220> FEATURE:
<221> NAME/KEY: misc_difference
<222> LOCATION: (3)..(4)
<223> OTHER INFORMATION: phosphorothioate bond
<220> FEATURE:
<221> NAME/KEY: misc_difference
<222> LOCATION: (5)..(6)
<223> OTHER INFORMATION: phosphorothioate bond
<220> FEATURE:
<221> NAME/KEY: modified_base
<222> LOCATION: (9)..(9)
<223> OTHER INFORMATION: um
<220> FEATURE:
<221> NAME/KEY: modified_base
<222> LOCATION: (12)..(12)
<223> OTHER INFORMATION: cm
<220> FEATURE:
<221> NAME/KEY: misc_difference
<222> LOCATION: (17)..(18)
<223> OTHER INFORMATION: phosphorothioate bond
<220> FEATURE:
<221> NAME/KEY: misc_difference
<222> LOCATION: (19)..(20)
<223> OTHER INFORMATION: phosphorothioate bond
<220> FEATURE:
<221> NAME/KEY: modified_base
<222> LOCATION: (20)..(21)
<223> OTHER INFORMATION: thymine deoxyribonucleotide (dT)
```

```
<220> FEATURE:
<221> NAME/KEY: misc_difference
<222> LOCATION: (20)..(21)
<223> OTHER INFORMATION: phosphorothioate bond

<400> SEQUENCE: 31 cguuggauu ccugaacaun n                                              21

<210> SEQ ID NO 32
<211> LENGTH: 21
<212> TYPE: RNA
<213> ORGANISM: Artificial Sequence
<220> FEATURE:
<223> OTHER INFORMATION: siRNA guide strand
<220> FEATURE:
<221> NAME/KEY: modified_base
<222> LOCATION: (2)..(2)
<223> OTHER INFORMATION: um
<220> FEATURE:
<221> NAME/KEY: modified_base
<222> LOCATION: (18)..(18)
<223> OTHER INFORMATION: 2'-O-methyl-adenosine
<220> FEATURE:
<221> NAME/KEY: modified_base
<222> LOCATION: (19)..(19)
<223> OTHER INFORMATION: gm
<220> FEATURE:
<221> NAME/KEY: misc_difference
<222> LOCATION: (19)..(20)
<223> OTHER INFORMATION: phosphorothioate bond
<220> FEATURE:
<221> NAME/KEY: modified_base
<222> LOCATION: (20)..(21)
<223> OTHER INFORMATION: thymine deoxyribonucleotide (dT)
<220> FEATURE:
<221> NAME/KEY: misc_difference
<222> LOCATION: (20)..(21)
<223> OTHER INFORMATION: phosphorothioate bond

<400> SEQUENCE: 32
auguucagga auccaacagn n                                             21

<210> SEQ ID NO 33
<211> LENGTH: 21
<212> TYPE: RNA
<213> ORGANISM: Artificial Sequence
<220> FEATURE:
<223> OTHER INFORMATION: siRNA passenger strand
<220> FEATURE:
<221> NAME/KEY: modified_base
<222> LOCATION: (20)..(21)
<223> OTHER INFORMATION: thymine deoxyribonucleotide (dT)

<400> SEQUENCE: 33
uaaggcuaug aagagauacn n                                             21

<210> SEQ ID NO 34
<211> LENGTH: 21
<212> TYPE: RNA
<213> ORGANISM: Artificial Sequence
<220> FEATURE:
<223> OTHER INFORMATION: siRNA guide strand
<220> FEATURE:
<221> NAME/KEY: modified_base
<222> LOCATION: (20)..(21)
<223> OTHER INFORMATION: thymine deoxyribonucleotide (dT)

<400> SEQUENCE: 34
guaucucuuc auagccuuan n                                             21

<210> SEQ ID NO 35
```

```
<211> LENGTH: 21
<212> TYPE: RNA
<213> ORGANISM: Artificial Sequence
<220> FEATURE:
<223> OTHER INFORMATION: siRNA passenger strand
<220> FEATURE:
<221> NAME/KEY: modified_base
<222> LOCATION: (1)..(1)
<223> OTHER INFORMATION: um
<220> FEATURE:
<221> NAME/KEY: misc_difference
<222> LOCATION: (1)..(2)
<223> OTHER INFORMATION: phosphorothioate bond
<220> FEATURE:
<221> NAME/KEY: modified_base
<222> LOCATION: (2)..(2)
<223> OTHER INFORMATION: 2'-O-methyl-adenosine
<220> FEATURE:
<221> NAME/KEY: misc_difference
<222> LOCATION: (2)..(3)
<223> OTHER INFORMATION: phosphorothioate bond
<220> FEATURE:
<221> NAME/KEY: modified_base
<222> LOCATION: (3)..(3)
<223> OTHER INFORMATION: 2'-O-methyl-adenosine
<220> FEATURE:
<221> NAME/KEY: misc_difference
<222> LOCATION: (3)..(4)
<223> OTHER INFORMATION: phosphorothioate bond
<220> FEATURE:
<221> NAME/KEY: misc_difference
<222> LOCATION: (5)..(6)
<223> OTHER INFORMATION: phosphorothioate bond
<220> FEATURE:
<221> NAME/KEY: modified_base
<222> LOCATION: (9)..(9)
<223> OTHER INFORMATION: um
<220> FEATURE:
<221> NAME/KEY: modified_base
<222> LOCATION: (12)..(12)
<223> OTHER INFORMATION: 2'-O-methyl-adenosine
<220> FEATURE:
<221> NAME/KEY: misc_difference
<222> LOCATION: (17)..(18)
<223> OTHER INFORMATION: phosphorothioate bond
<220> FEATURE:
<221> NAME/KEY: misc_difference
<222> LOCATION: (19)..(20)
<223> OTHER INFORMATION: phosphorothioate bond
<220> FEATURE:
<221> NAME/KEY: modified_base
<222> LOCATION: (20)..(21)
<223> OTHER INFORMATION: thymine deoxyribonucleotide (dT)
<220> FEATURE:
<221> NAME/KEY: misc_difference
<222> LOCATION: (20)..(21)
<223> OTHER INFORMATION: phosphorothioate bond

<400> SEQUENCE: 35
uaaggcuaug aagagauacn n                                          21

<210> SEQ ID NO 36
<211> LENGTH: 21
<212> TYPE: RNA
<213> ORGANISM: Artificial Sequence
<220> FEATURE:
<223> OTHER INFORMATION: siRNA guide strand
<220> FEATURE:
<221> NAME/KEY: modified_base
<222> LOCATION: (2)..(2)
<223> OTHER INFORMATION: um
<220> FEATURE:
<221> NAME/KEY: modified_base
<222> LOCATION: (18)..(18)
<223> OTHER INFORMATION: um
<220> FEATURE:
<221> NAME/KEY: modified_base
```

```
<222> LOCATION: (19)..(19)
<223> OTHER INFORMATION: 2'-O-methyl-adenosine
<220> FEATURE:
<221> NAME/KEY: misc_difference
<222> LOCATION: (19)..(20)
<223> OTHER INFORMATION: phosphorothioate bond
<220> FEATURE:
<221> NAME/KEY: modified_base
<222> LOCATION: (20)..(21)
<223> OTHER INFORMATION: thymine deoxyribonucleotide (dT)
<220> FEATURE:
<221> NAME/KEY: misc_difference
<222> LOCATION: (20)..(21)
<223> OTHER INFORMATION: phosphorothioate bond

<400> SEQUENCE: 36
guaucucuuc auagccuuan n                                             21
```